(12) United States Patent
Moore

(10) Patent No.: US 11,865,003 B2
(45) Date of Patent: Jan. 9, 2024

(54) EXTERNAL HYDRAULICALLY ERECTABLE PHALLUS PROSTHETIC DEVICE

(71) Applicant: VDOM LLC, Mableton, GA (US)

(72) Inventor: Glenise Moore, Atlanta, GA (US)

(73) Assignee: VDOM LLC, Mableton, GA (US)

( * ) Notice: Subject to any disclaimer, the term of this patent is extended or adjusted under 35 U.S.C. 154(b) by 0 days.

(21) Appl. No.: 18/110,807

(22) Filed: Feb. 16, 2023

(65) Prior Publication Data

US 2023/0255774 A1    Aug. 17, 2023

Related U.S. Application Data

(60) Provisional application No. 63/310,938, filed on Feb. 16, 2022.

(51) Int. Cl.
*A61H 19/00* (2006.01)
*A61F 2/26* (2006.01)

(52) U.S. Cl.
CPC ...................................... *A61F 2/26* (2013.01)

(58) Field of Classification Search
CPC ........... A61F 2/26; A61H 19/34; A61H 19/40; A61H 19/44; A61H 2205/087; A61H 23/04; A61H 9/005; Y10S 601/16
USPC ........................................................... 600/40
See application file for complete search history.

(56) References Cited

U.S. PATENT DOCUMENTS

| | | | |
|---|---|---|---|
| 9,089,469 B2 * | 7/2015 | Dees | A63F 9/0611 |
| 2003/0114729 A1 * | 6/2003 | Forsell | A61F 2/26 600/38 |
| 2011/0201880 A1 * | 8/2011 | Fogarty | A61F 2/26 600/40 |
| 2022/0249943 A1 * | 8/2022 | Poole | A63F 9/00 |

* cited by examiner

*Primary Examiner* — Samuel G Gilbert
(74) *Attorney, Agent, or Firm* — Padowithz Alce; Alce PLLC

(57) ABSTRACT

Systems and apparatuses of an electro-mechanical phallus prosthetic device includes a source reservoir that, at rest, stores a liquid; a target reservoir that, in use, flexibly stores at least a portion of the liquid; a manifold housing including a first chamber that includes a plurality of flow paths arranged between the source reservoir and the target reservoir that, in use, act as conduits that transport the liquid through the manifold housing; and a second chamber that houses an electro-mechanical pump that, in use, forces a movement of the liquid from the source reservoir through at least one inlet flow path of the plurality of flow paths to the target reservoir.

21 Claims, 16 Drawing Sheets

EXTERNAL HYDRAULICALLY ERECTABLE PHALLUS PROSTHETIC DEVICE

CROSS-REFERENCE TO RELATED APPLICATIONS

This application claims the benefit of U.S. Provisional Application No. 63/310,938, filed 16 Feb. 2022, which is incorporated herein in its entirety by this reference.

TECHNICAL FIELD(S)

This invention relates generally to the human prosthetic device field, and more specifically to a new and useful system and apparatus for a prosthetic phallus and method for implementing a prosthetic phallus in the human prosthetic device field.

BACKGROUND

Currently, prosthetic phallus technology involves the implanting of prosthetic phallus devices or components. Such a process involves invasive medical and surgical procedures. In addition, traditional erectile facilitation technology requires the regular use of medication and requires scheduling and timing medication dosages to facilitate an erectile process at a desired time.

While the use of traditional prosthetic phallus devices and erectile facilitation technology may be useful for facilitating some erectile processes at limited or set times, the nature of these traditional approaches are restrictive in the need for a user to undergo invasive surgical procedures and/or the need for a user to take regular doses of medication.

Accordingly, there is a need in the human prosthetic device field for a wearable non-invasive prosthetic phallus device that can be used without the need to undergo invasive surgery, and preferably can be used to provide or facilitate an erectile process on-demand when desired by a user, without the need for medication.

One or more embodiments of the present application include a wearable non-invasive prosthetic phallus that may attach to custom under garments (e.g., underwear), allowing the individual to wear it throughout daily activities. With the ability to control the device with buttons on the device, or by connected electronics over wireless communication, the wearer is enabled to create an erection and enable times of intimacy at will, which provides the user with an unencumbered sexual encounter during intimacy. In such embodiments, the wearable non-invasive prosthetic phallus essentially enables the user to have an on-demand erection without the need to stop to assemble parts, wait for medication to activate, or consider surgical procedures which could have risks, complications, or the need for revision surgery.

The below-described embodiments of the present application herein provide technical solutions that address, at least the need(s) described above.

BRIEF SUMMARY OF THE INVENTION(S)

In one embodiment, an electro-mechanical phallus prosthetic device includes a source reservoir that, at rest, stores a liquid; a target reservoir that, in use, flexibly stores at least a portion of the liquid; a manifold housing including a first chamber that includes a plurality of flow paths arranged between the source reservoir and the target reservoir that, in use, act as conduits that transport the liquid through the manifold housing; and a second chamber that houses an electro-mechanical pump that, in use, forces a movement of the liquid from the source reservoir through at least one inlet flow path of the plurality of flow paths to the target reservoir.

In one embodiment, the source reservoir is mechanically secured along a first side of the manifold housing; the target reservoir is mechanically secured along a second side of the manifold housing that is perpendicular or substantially perpendicular to the first side; and the device further includes a prosthetic phallus appendage that encompasses the target reservoir, the manifold housing, and the source reservoir.

In one embodiment, in use: the source reservoir elastically deforms to provide the fluid into the first chamber of the manifold housing based on an application of the electro-mechanical pump; and the target reservoir flexibly expands into a shaft of the prosthetic phallus appendage based on storing the fluid from the source reservoir.

In one embodiment, the at least one inlet flow path comprises a tubular shape that extends from a pump outlet to a fluid inlet of the target reservoir.

In one embodiment, the plurality of flow paths includes one or more outlet flow paths comprising one or more tubular shapes that extend from one or more fluid outlets of the target reservoir to a fluid inlet of the source reservoir.

In one embodiment, the plurality of flow paths includes a plurality of outlet flow paths, wherein each of the plurality of outlet flow paths comprises a tubular shape, the plurality of outlet flow paths extending from one or more fluid outlets of the target reservoir merge at a point within the manifold housing to form a single outlet flow path to at least one fluid inlet of the source reservoir.

In one embodiment, when the manifold housing is in a normal state relative to a horizontally plane, the at least one flow path is positioned at a height greater that is normal to the horizontally plane relative to a height of the one or more outlet flow paths.

In one embodiment, the device further includes a first aperture between the first chamber and the second chamber that receives a pump inlet of the electro-mechanical pump; and a second aperture between the first chamber and the second chamber that receives a pump outlet of the electro-mechanical pump.

In one embodiment, the first aperture and the second aperture are arranged along a same chamber wall between the first chamber and the second chamber.

In one embodiment, the electro-mechanical pump when arranged within the second chamber of the manifold housing and the pump inlet and the pump outlet are engaged with the first aperture and the second aperture creates a one-way fluid channel that passes liquid from the source reservoir to the target reservoir.

In one embodiment, the device further includes a fabric sheath that extends from a fluid inlet of the target reservoir and that encompasses a body of the target reservoir.

In one embodiment, a proximal end of the fabric sheath is secured to the manifold housing via a circumferential lip of a circumferential spout extending from a body of the manifold housing.

In one embodiment, the manifold housing comprises a single three-dimensionally printed continuously integrated component.

In one embodiment, the device further includes a check valve that is arranged between a pump outlet of the electro-mechanical pump and the at least one inlet flow path to the target reservoir.

In one embodiment, the device further includes an electromechanical valve that is arranged between the one or more fluid outlets of the target reservoir and the fluid inlet of the source reservoir.

In one embodiment, the device further includes a manifold lid that is mechanically secured to the manifold housing and that covers the second chamber of the manifold housing.

In one embodiment, the device further includes a prosthetic phallus appendage that houses the target reservoir, the manifold housing, and the source reservoir.

In one embodiment, a device includes a source reservoir that, at rest, stores a liquid, wherein the source reservoir is mechanically coupled along a first side of a manifold housing; a target reservoir that, in use, flexibly stores at least a portion of the liquid and expands along an extent of a shaft based on the portion of the liquid that is stored within the target reservoir; a manifold housing including: a first chamber that includes a plurality of flow paths arranged between the source reservoir and the target reservoir that, in use, move the liquid through the manifold housing; and a second chamber that houses an electro-mechanical pump that, in use, forces a movement of the liquid from the source reservoir through a source flow path of the plurality of flow paths to the target reservoir; and a prosthetic appendage that houses the target reservoir, the manifold housing, and the source reservoir.

In one embodiment, the source flow path extends from a pump outlet of the electro-mechanical pump to a fluid inlet of the target reservoir.

In one embodiment, the plurality of flow paths includes one or more drainage flow paths that extend from one or more fluid outlets of the target reservoir to a fluid inlet of the source reservoir.

In one embodiment, a device includes a source reservoir that, at rest, stores a liquid, wherein the source reservoir is mechanically coupled along a first side of a manifold housing; a target reservoir that, in use, flexibly stores at least a portion of the liquid and expands along an extent of a shaft based on the portion of the liquid that is stored within the target reservoir; a manifold housing including: a first chamber that includes a plurality of flow paths arranged between the source reservoir and the target reservoir that, in use, move the liquid through the manifold housing; and multiple independent or connected chambers or orifices that house the individual components of an electro-mechanical pump, comprising an electric motor, gears, shafts, and a suction chamber or a hydraulic working chamber, that, in use, forces a movement of the liquid from the source reservoir through a source flow path of the plurality of flow paths to the target reservoir; and a prosthetic appendage that houses the target reservoir, the manifold housing, and the source reservoir.

DESCRIPTION OF THE PREFERRED EMBODIMENTS

Figure 1A:
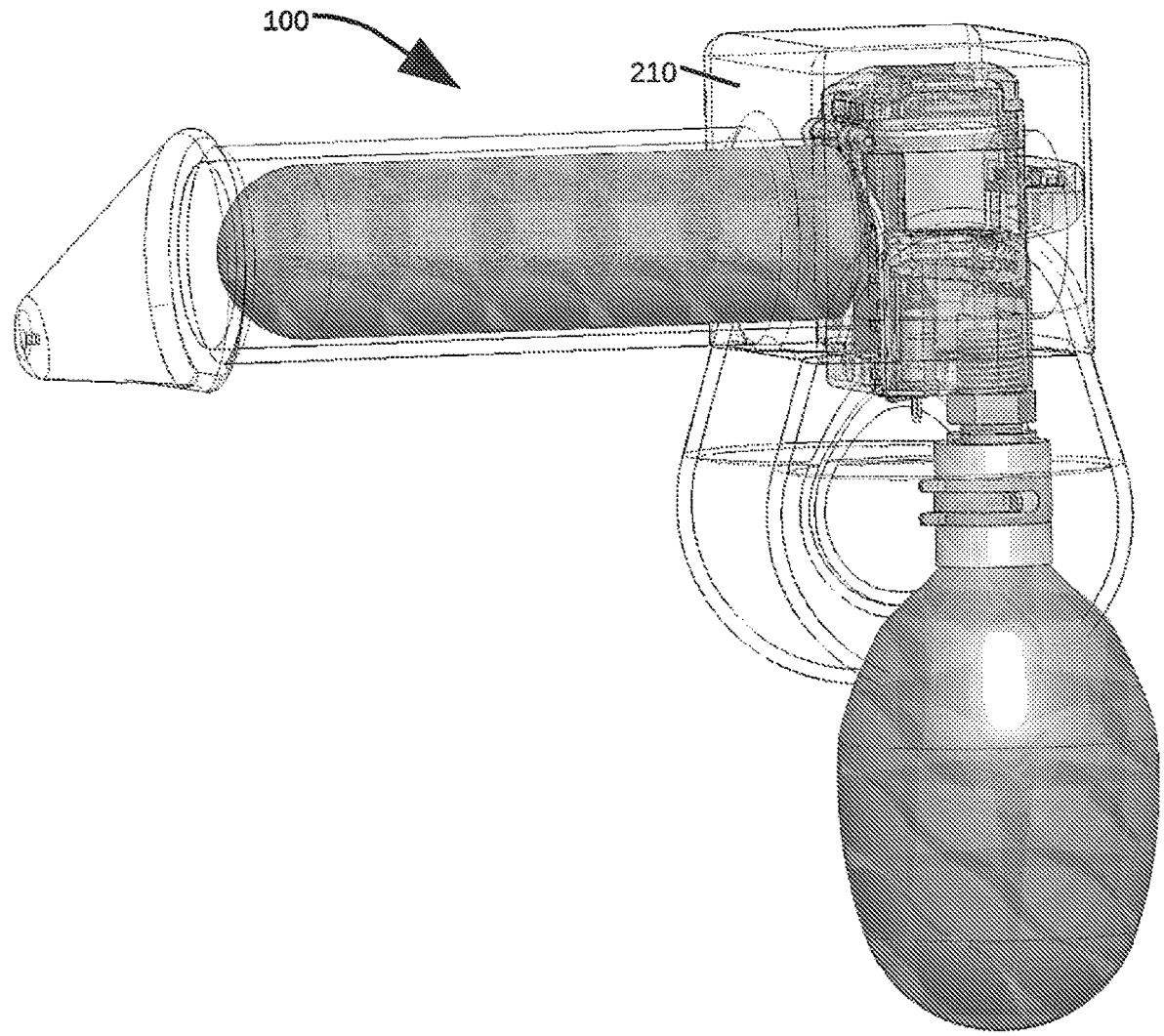
FIGS. 1A-1C illustrate a first embodiment of a phallus prosthetic device in accordance with one or more embodiments of the present application.
Figure 1B:
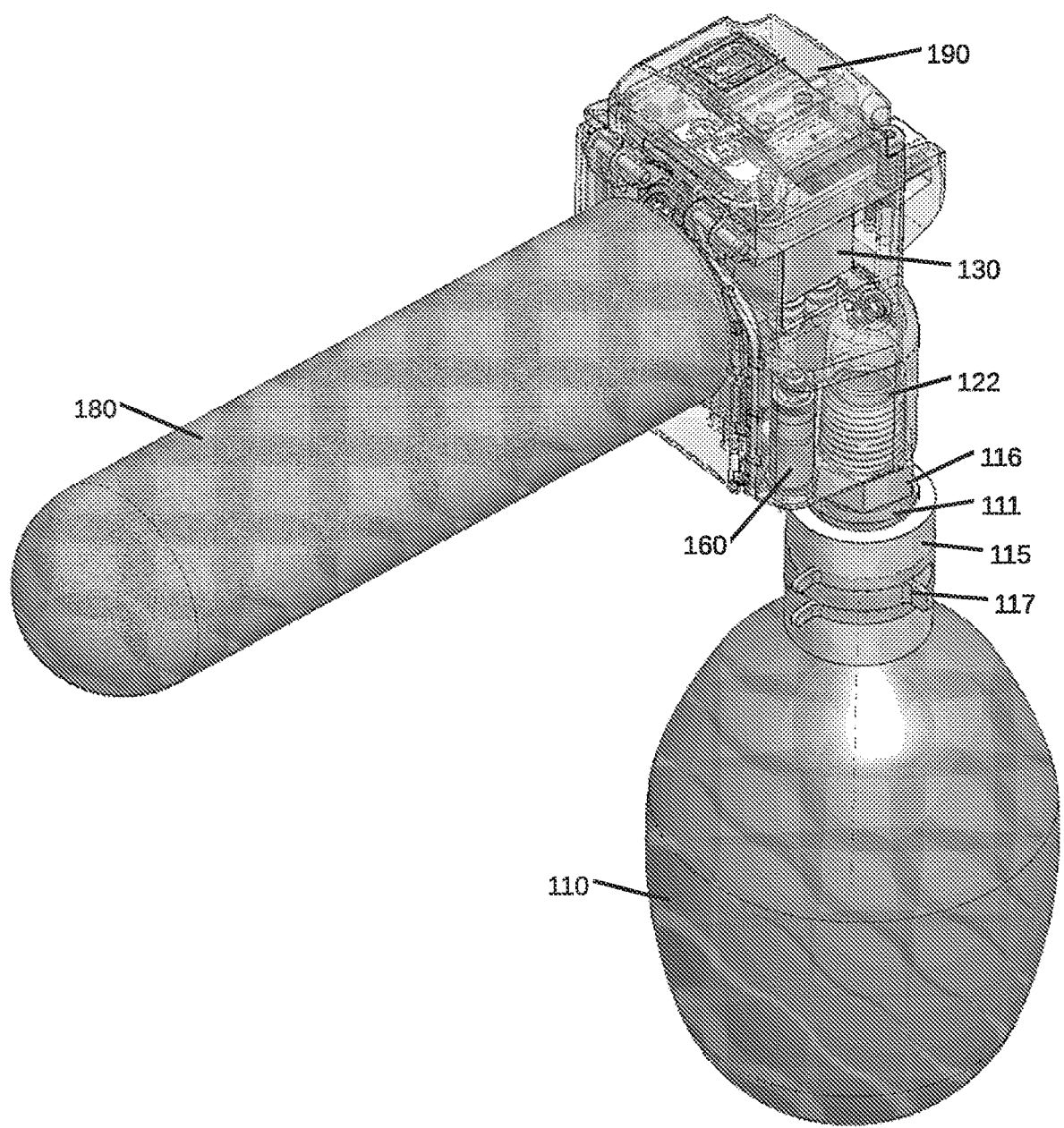
Figure 1C:
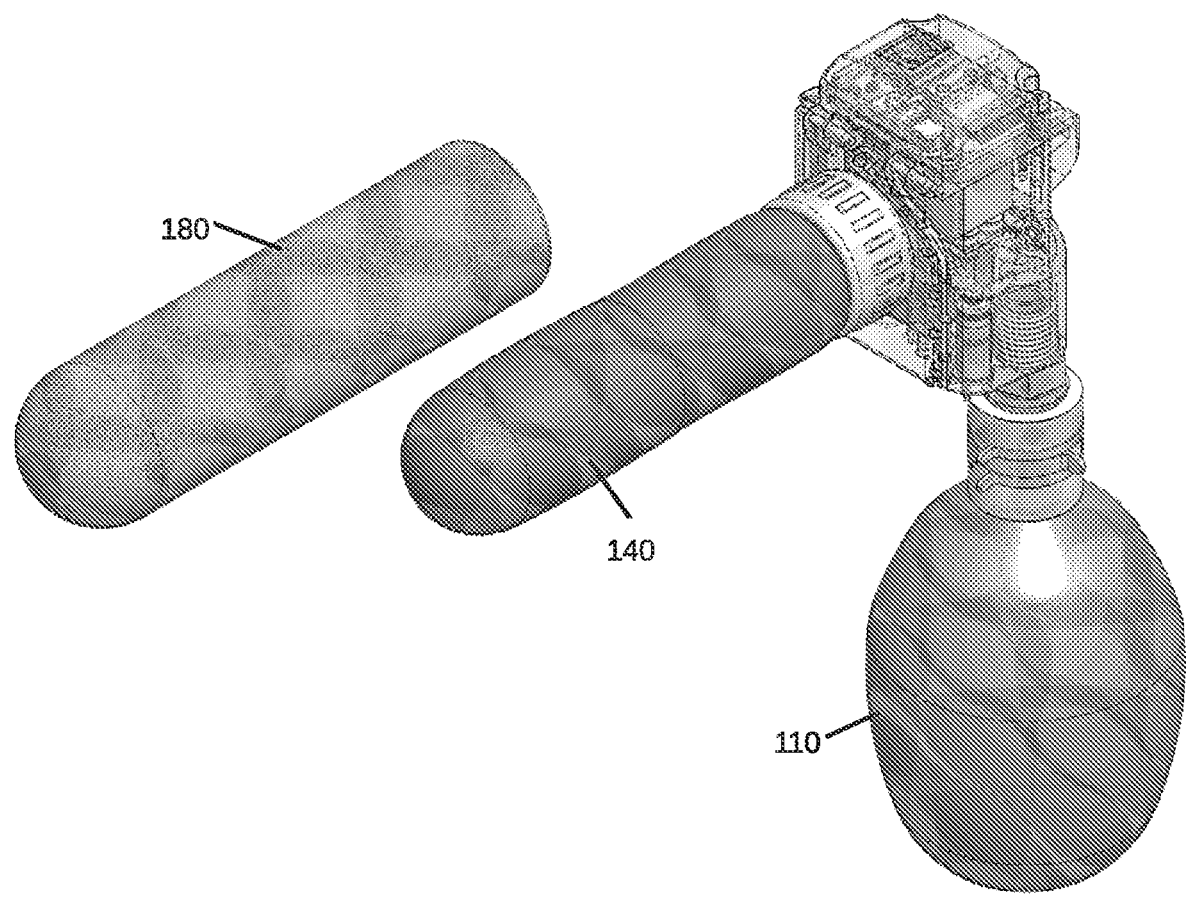
Figure 2:
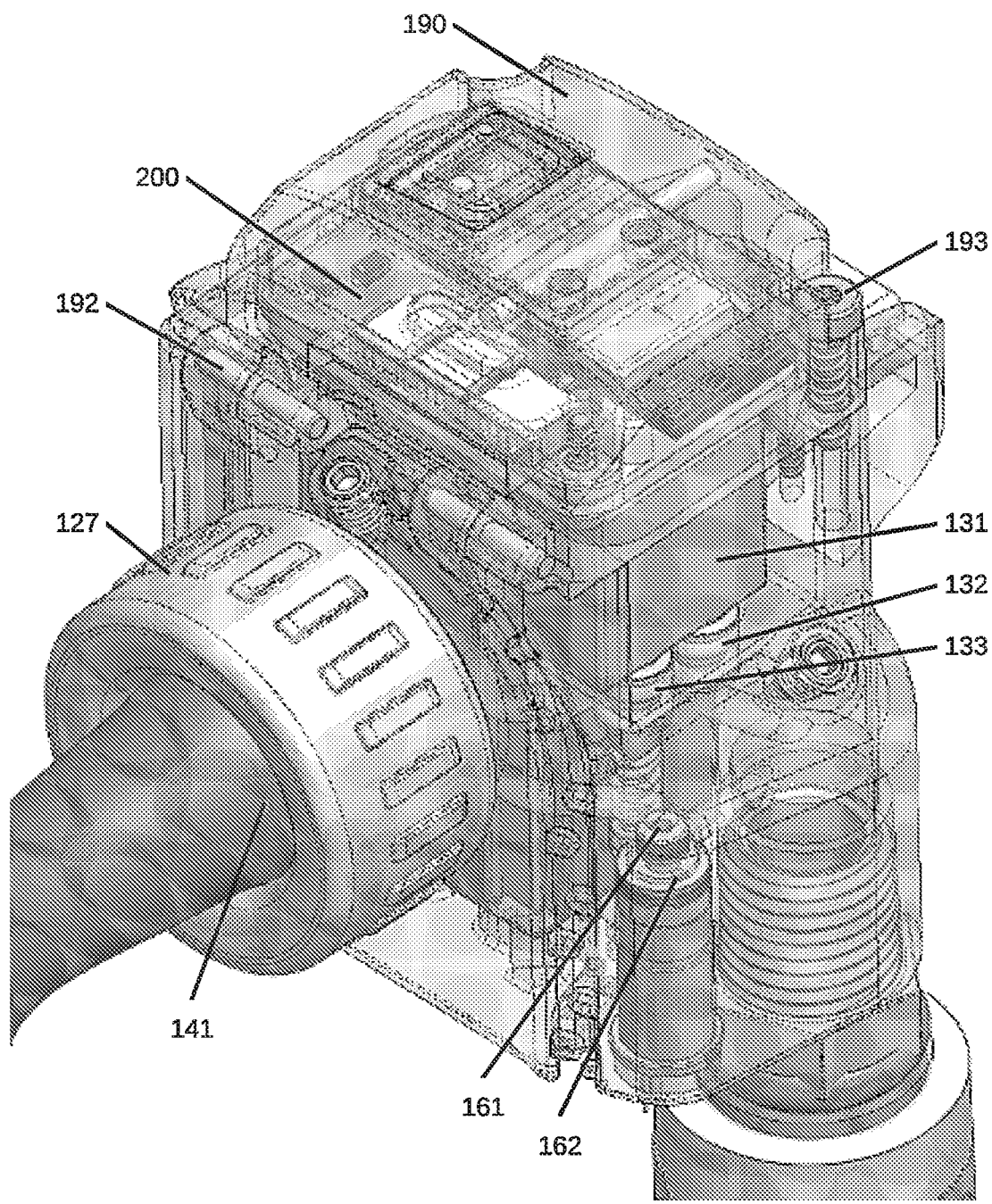
FIG. 2 illustrates a first embodiment of a phallus prosthetic device in accordance with one or more embodiments of the present application.
Figure 3:
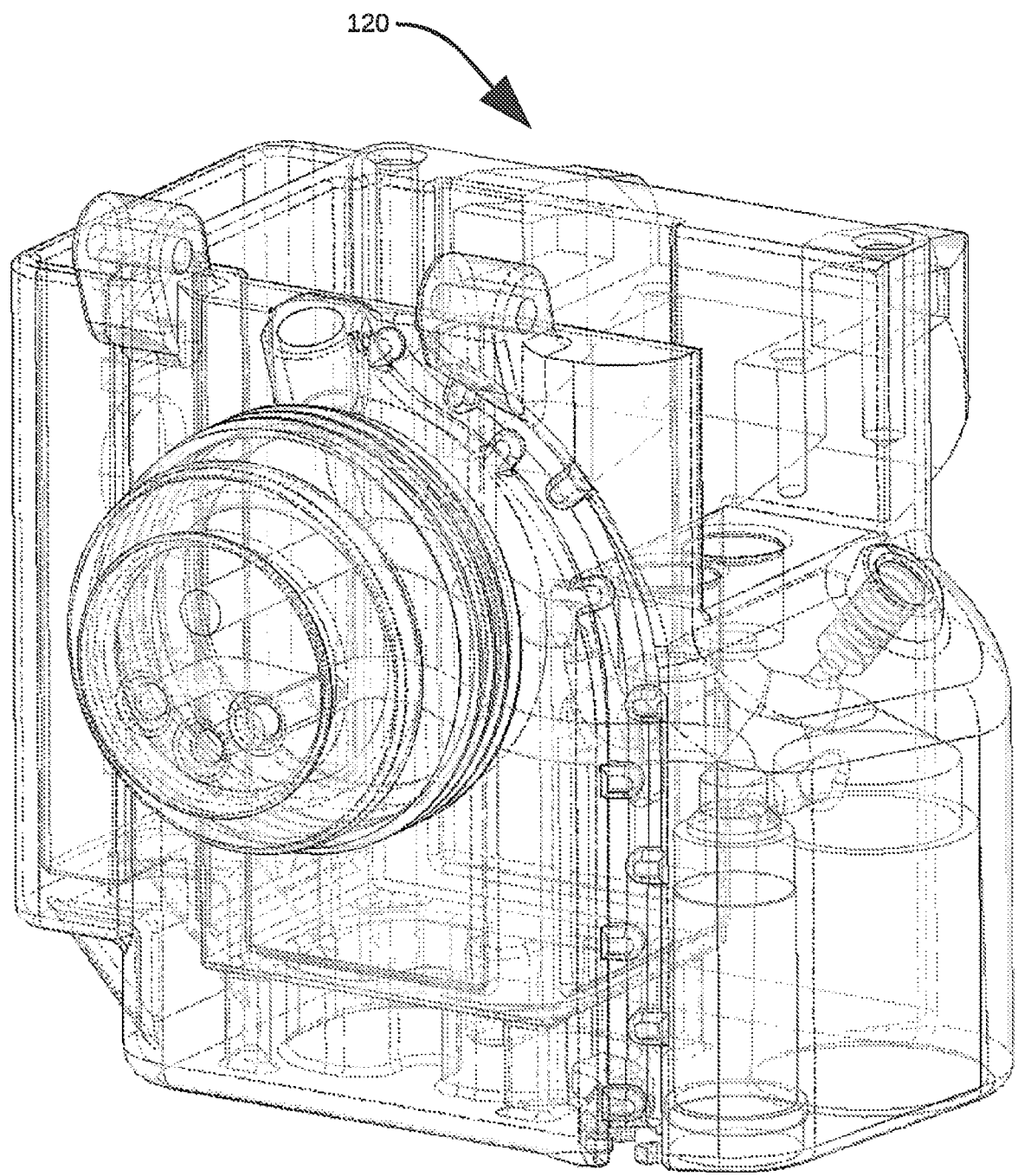
FIG. 3 illustrates a first embodiment of a manifold of a phallus prosthetic device in accordance with one or more embodiments of the present application.
Figure 4A:
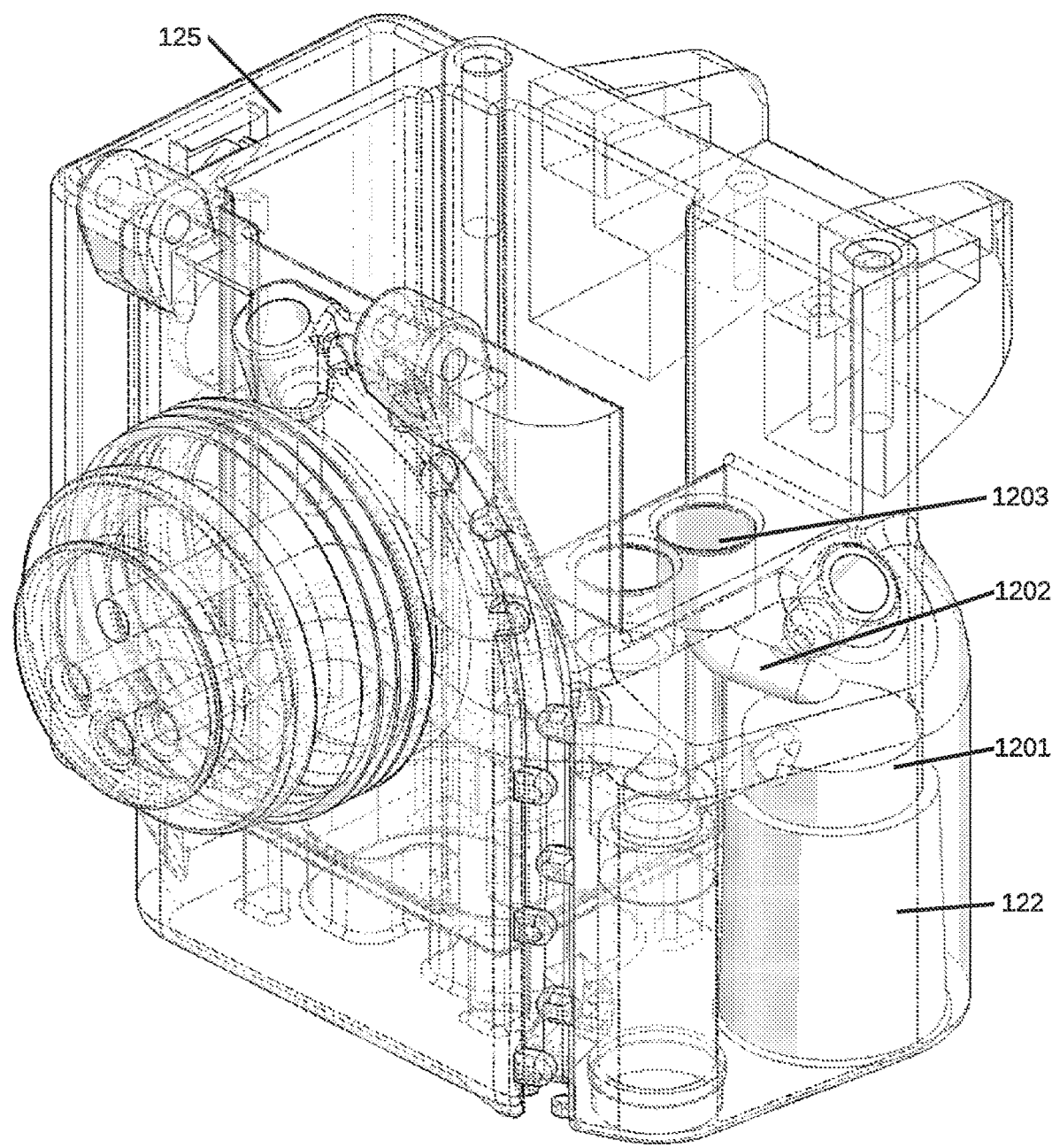
FIGS. 4A-4D illustrate a first embodiment of a manifold of a phallus prosthetic device in accordance with one or more embodiments of the present application.
Figure 4B:
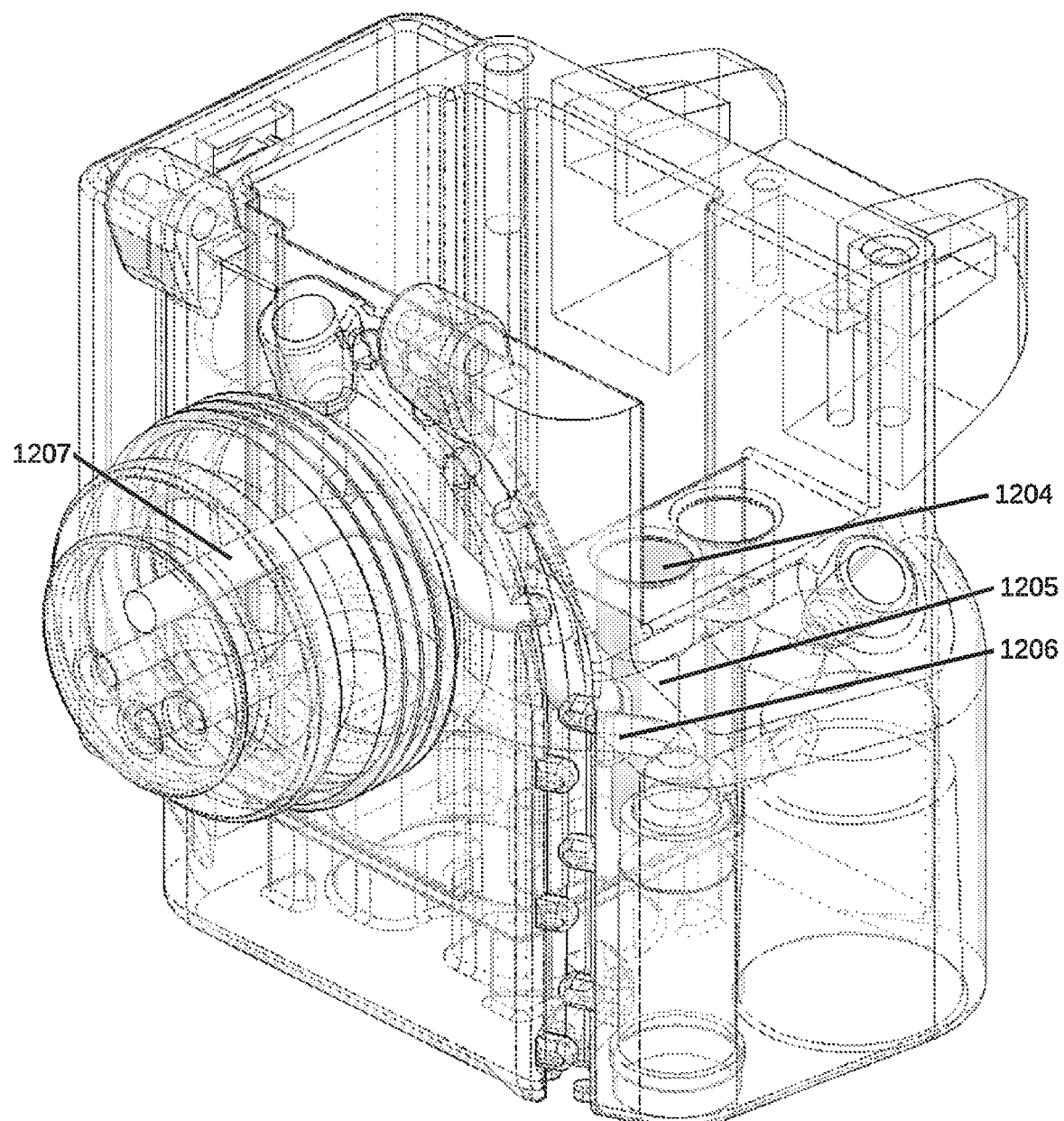
Figure 4C:
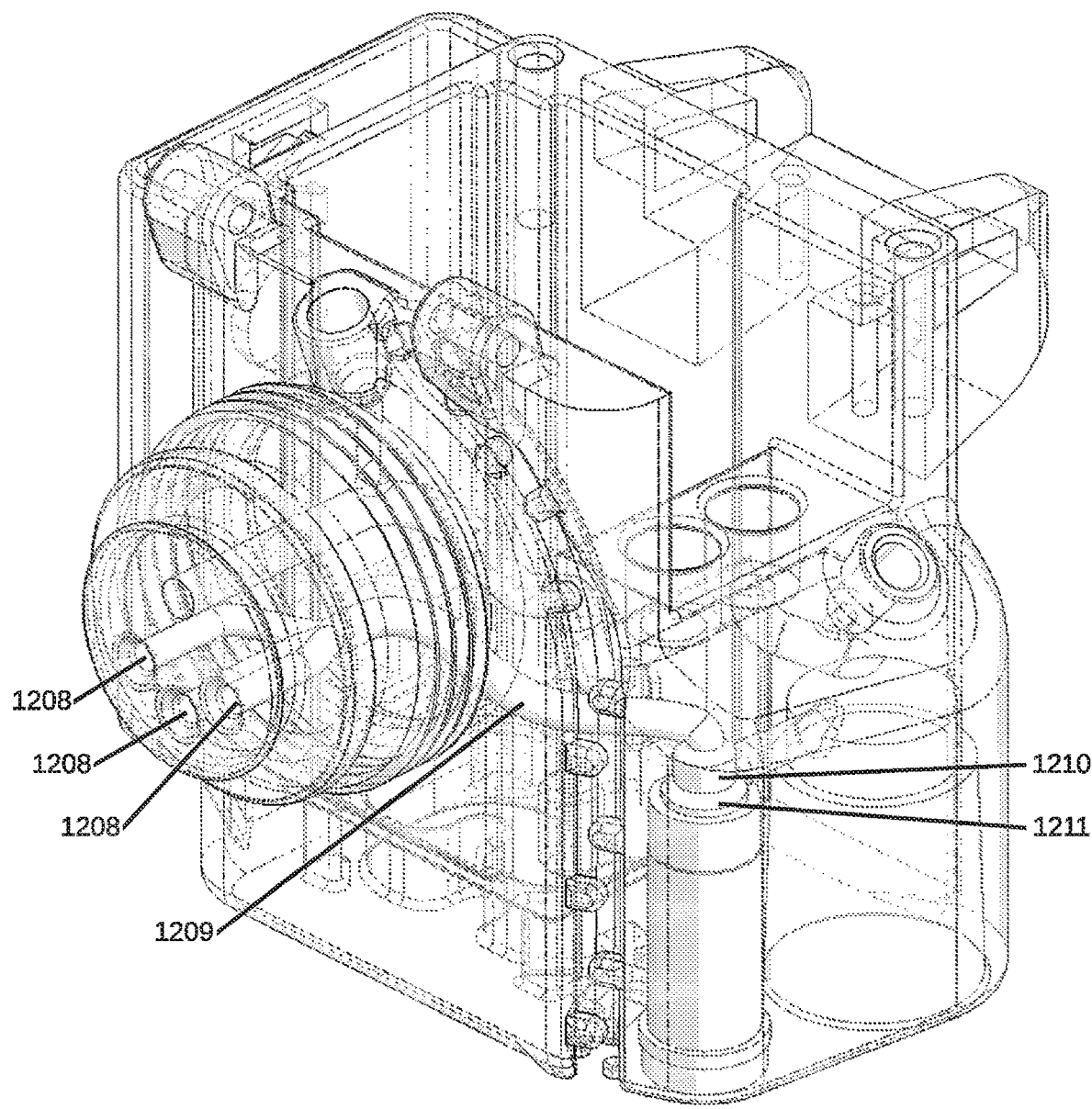
Figure 4D:
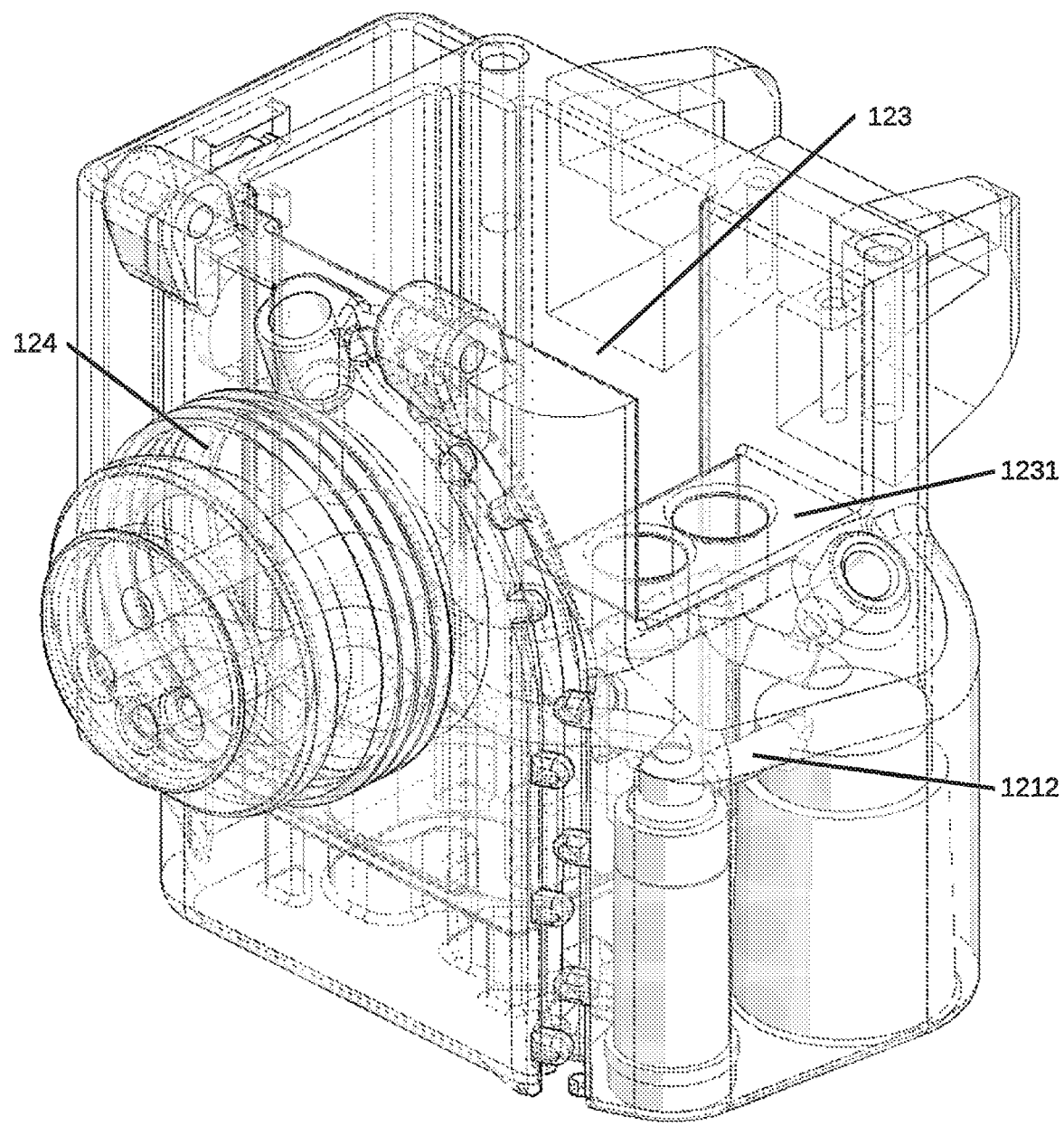
Figure 5A:
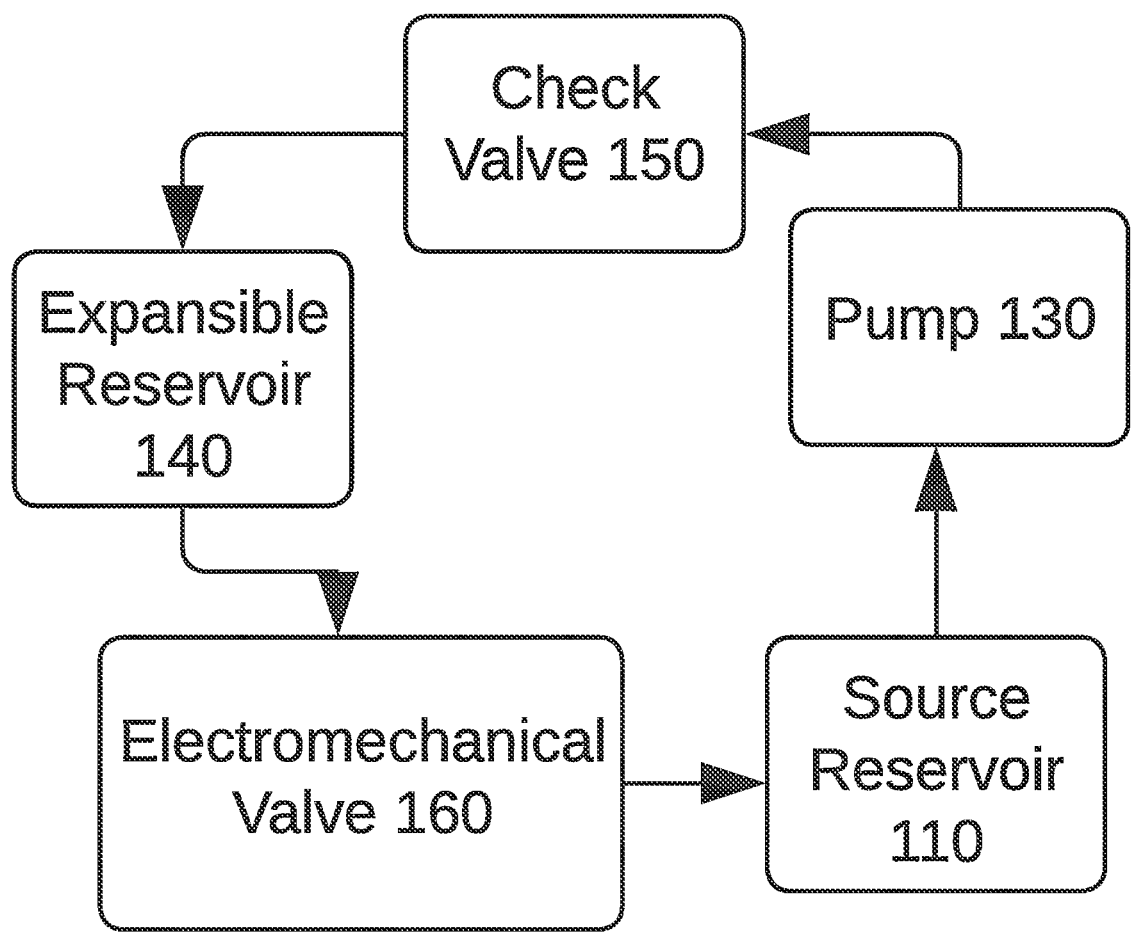
FIGS. 5A-5B illustrate example schematics of possible flow diagrams of a phallus prosthetic device in accordance with one or more embodiments of the present application.
Figure 5B:
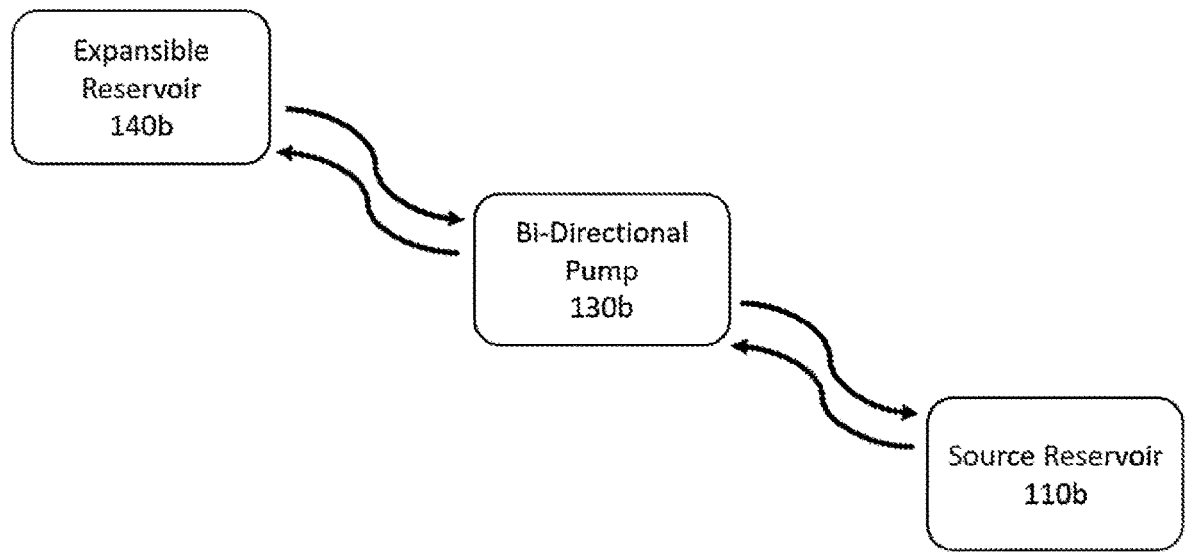
Figure 6A:
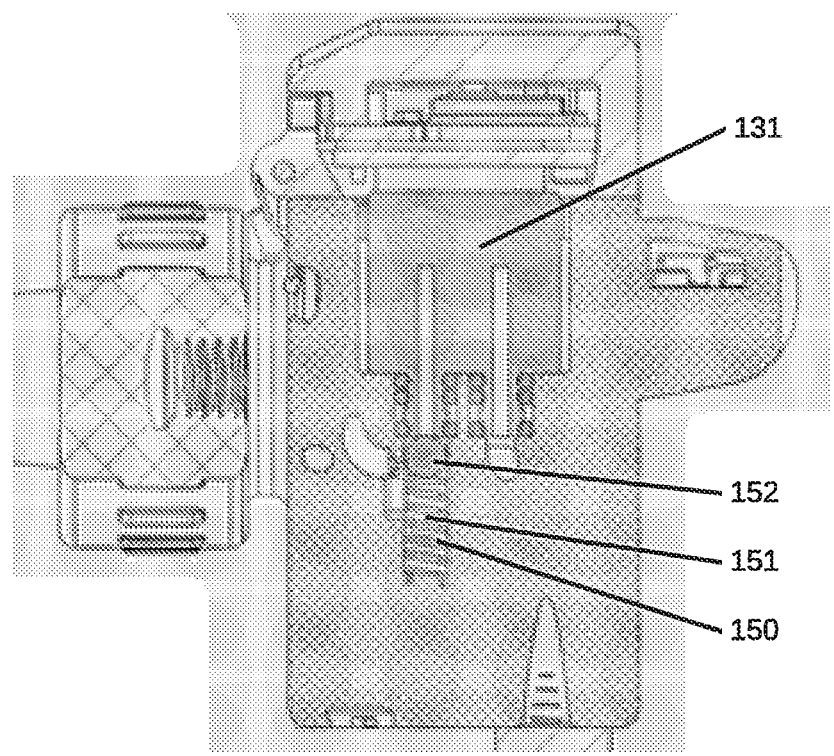
FIGS. 6A-6B illustrate a first embodiment of a phallus prosthetic device in accordance with one or more embodiments of the present application.
Figure 6B:
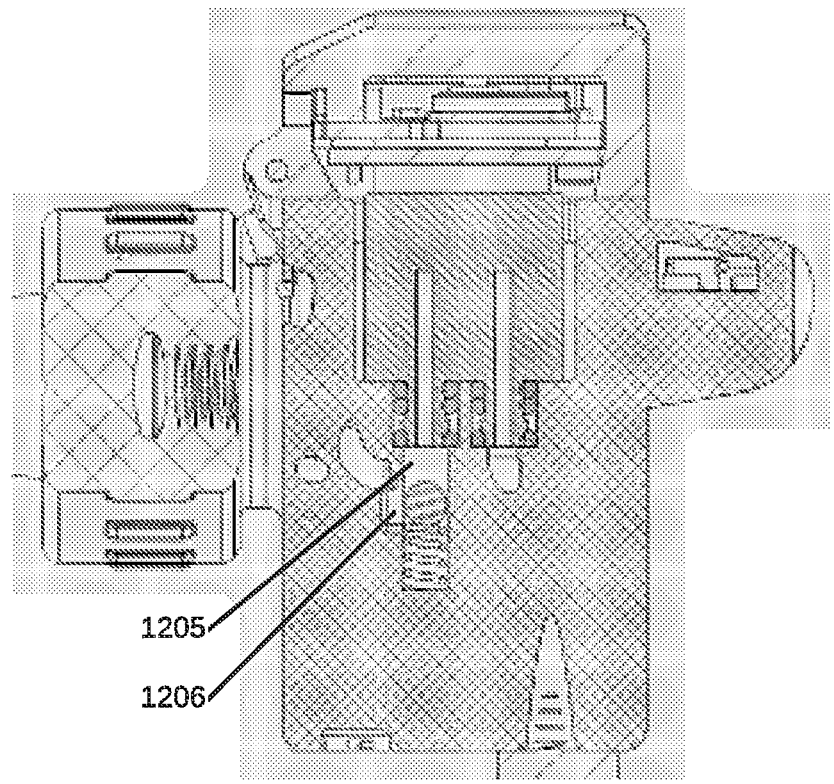
Figure 7C:
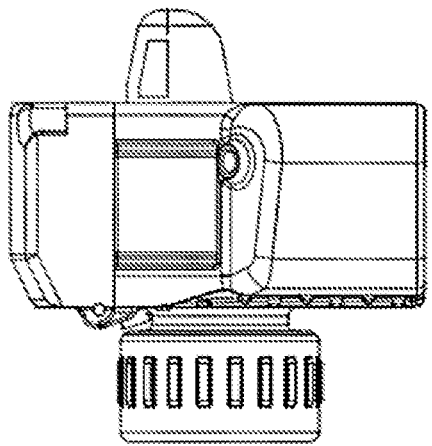
FIGS. 7A-7E illustrate a first embodiment of a phallus prosthetic device in accordance with one or more embodiments of the present application.
Figure 7B:
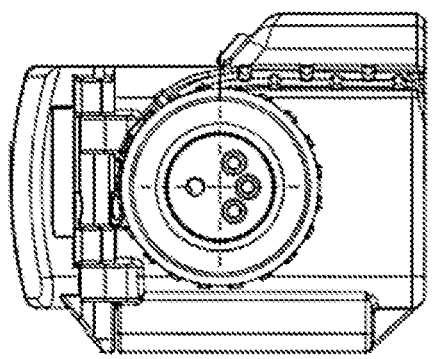
Figure 7A:
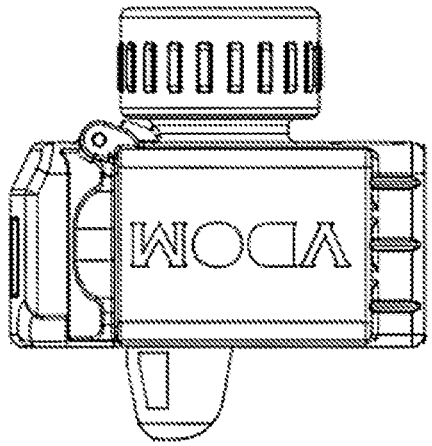
Figure 7E:
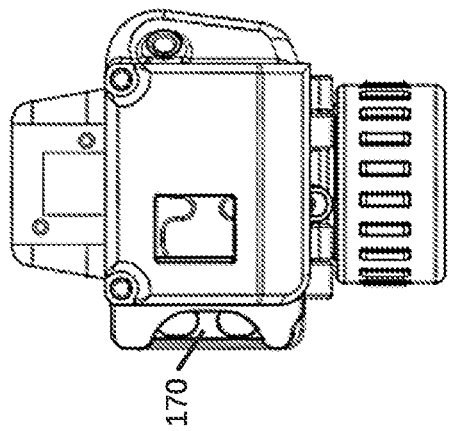
Figure 7D:
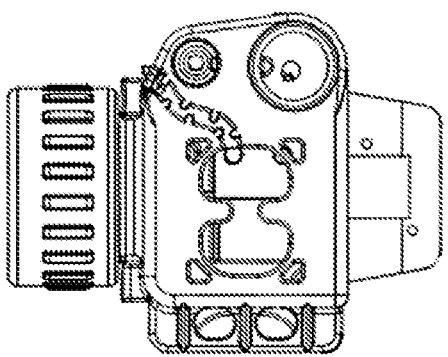

The following description of the preferred embodiments of the present application are not intended to limit the inventions to these preferred embodiments, but rather to enable any person skilled in the art to make and use these inventions.

1.00 Phallus Prosthetic Device

As shown in FIGS. 1-10, a male phallus prosthetic device 100 includes a source reservoir no, a flow-regulating manifold 120, a pump 130, an expansible reservoir 140, an electromechanical valve 160, and a manifold cover 190. In some embodiments, male prosthetic device 100 may also include a check valve 150, a battery 170, a sleeve 180, controller 200, and prosthetic enclosure 210. In operation of a preferred embodiment of male prosthetic device 100, male prosthetic device 100 may include a closed-loop hydraulic circuit for fluid flow from, to, and through one or more components of male prosthetic device 100, as shown by way of example in FIGS. 5A-5B.

1.10 Male Prosthetic Device: Source Reservoir

In a preferred embodiment, source reservoir no of male prosthetic device 100 may function to receive, store, and supply working fluid. Source reservoir 110 may be coupled to and fluidly connected to manifold 120 by a hydraulic coupling 115. In some embodiments, source reservoir no may be a flexible reservoir made of an elastomeric material.

In some embodiments, source reservoir no may store fluid in a rest state of male prosthetic device 100, supply fluid to expansible reservoir 140 in an expanding state of male prosthetic device 100 and receive fluid from expansible reservoir 140 in a contracting state of male prosthetic device 100.

In an implementation, source reservoir no may be made of a flexible and/or resilient material, such as an elastomeric material. In some embodiments, source reservoir 110 may be a flexible balloon-type reservoir. Source reservoir no may include an opening in that allows bi-directional fluid flow into and out of source reservoir no.

Preferably, source reservoir no may provide a supply of working fluid for male prosthetic device 100. In use, a pumping mechanism may induce a flow of fluid from source reservoir no to flow into and/or through one or more components of male prosthetic device 100. In some implementations, source reservoir no may contract when supplying fluid. In use, source reservoir no may receive working fluid from one or more components of male prosthetic device 100. In some embodiments, source reservoir 110 may expand when receiving a flow of fluid.

Preferably, opening in of source reservoir 110 may be coupled mechanically and fluidly to manifold 120 by a hydraulic coupling 115, as shown by way of example in FIGS. 1A-1C and FIG. 2. In one implementation, hydraulic coupling 115 may include a threaded hydraulic coupling or fitting 116 and a clamp 117 (e.g., a hose clamp) for clamping opening in of source reservoir 110 onto the threaded hydraulic coupling. The threaded hydraulic coupling 116 may include a threaded section on an outer circumferential surface received concentrically within a correspondingly threaded hole 122 in manifold 120. Alternatively, threaded hydraulic coupling 116 may be threaded on an inner circumferential surface and threaded onto a threaded shaft of manifold 120 such that threaded hydraulic coupling 116 is concentrically outside of the threaded shaft of manifold 120. Alternatively, other sealed hydraulic connection may be utilized by one of ordinary skill in the art. For example, instead of a threaded connection, source reservoir 110 may be coupled to manifold 120 by a contracting plastic system such as a PEXa or PEXb system, or in an embodiment, an overlaid ORing system. In one implementation, hydraulic coupling 115 may alternatively include a standard hose clamp system such as commonly found in automotive applications. In another preferred embodiment, hydraulic coupling 115 may include a compression fitting in a manner similar to one found on a water-supply in a refrigerator.

1.20 Male Prosthetic Device: Flow-Regulating Manifold

In a preferred embodiment, male prosthetic device 100 includes a flow-regulating manifold 120 (manifold 120) that may function to mechanically and fluidly couple one or more components of male prosthetic device 100. In such a preferred embodiment, the manifold 120 may include a plurality of fluid passages, chambers, and ports that may define at least one hydraulic circuit for regulating and optimizing pressure in a flow of working fluid in male prosthetic device 100, as shown by way of example in FIG. 3 and FIGS. 4A-4D. In some embodiments, manifold 120 may also include a reservoir coupling cavity 122, a pump housing cavity 123 which may house pump 130, and a battery housing cavity 125 which may house battery 170.

Preferably, manifold 120 may be manufactured by an additive manufacturing process, such as 3-D printing or the like. In such a preferred embodiment, the construction of complex internal features of manifold 120, such as fluid passages, chambers, and ports 1201-1212 (described in section 1.20.0-1.20.12 below) may be facilitated by using an additive manufacturing process to manufacture manifold 120. In some embodiments, manifold 120 may be a single integral unitary structure. Such a unitary construction may advantageously allow for improved sealing and reduced leakage in hydraulic features of manifold 120. Alternatively, manifold 120 may be constructed from a plurality of separable parts secured together.

1.20.0 Flow-Regulating Manifold: Hydraulic Circuit

In a preferred embodiment, manifold 120 may include a plurality of fluid passages, chambers, and ports that may be fluidly connected to at least partially define at least one hydraulic circuit 1200. In such a preferred embodiment, manifold 120 may include a reservoir exchange chamber 1201, a pump inlet passage 1202, a pump inlet port 1203, a pump outlet port 1204, a first pump outlet chamber 1205, a second pump outlet chamber 1206, a reservoir inlet passage 1207, one or more reservoir outlet ports 1208, a reservoir outlet passage 1209, a valve inlet chamber 1210, a valve outlet chamber 1211, and a reservoir exchange passage 1212.

1.20.1 Hydraulic Circuit: Reservoir Exchange Chamber

In a preferred embodiment, manifold 120 may include a reservoir exchange chamber 1201 which may be a chamber adjacent to reservoir coupling hole 122. In such an embodiment, reservoir exchange chamber 1201 may be a fluid chamber that may allow fluid to flow or be exchanged between a reservoir of working fluid (e.g., source reservoir no) and one or more components of male prosthetic device 100. In an embodiment, reservoir exchange chamber 1201 may include a lower cylindrical wall with an opening adjacent the reservoir of working fluid and an upper frustoconical wall. In such an embodiment, "lower" may refer to a direction along a central longitudinal axis of reservoir exchange chamber 1201 toward the reservoir of fluid, and "upper" may refer to a direction along the central longitudinal axis away from the reservoir of fluid. In such an implementation, reservoir exchange chamber 1201 may include a radial inlet relative to the central longitudinal axis of reservoir chamber 1201 and an axial outlet relative to the central longitudinal axis. The radial inlet may be partially located on the lower cylindrical wall of reservoir exchange chamber 1201, and the axial outlet may be arranged in the upper frustoconical wall of reservoir exchange chamber 1201. The axial outlet of reservoir exchange chamber 1201 may allow a flow of working fluid from reservoir exchange chamber 1201 to pump inlet passage 1202.

1.20.2 Hydraulic Circuit: Pump Inlet Passage

In a preferred embodiment, manifold 120 may include a pump inlet passage 1202 that may function to guide working fluid from reservoir exchange chamber 1201 to an inlet port for a pumping mechanism for pumping the working fluid. Preferably, pump inlet passage 1202 may be fluidly coupled in series to and downstream of the outlet of reservoir exchange chamber 1201. Pump inlet passage 1202 may include an inlet at reservoir exchange chamber 1201, and an outlet at an inlet port of the pumping mechanism.

1.20.3 Hydraulic Circuit: Pump Inlet Port

In a preferred embodiment, manifold 120 may include a pump inlet port 1203 fluidly coupled in series to the outlet of pump inlet passage 1202. Pump inlet port 1203 may function to fluidly couple manifold 120 to an inlet nozzle of a pumping mechanism for pumping working fluid. In a first implementation, pump inlet port 1203 may include a cylindrical wall for housing the inlet nozzle of the pumping mechanism concentrically within the cylindrical wall. In such an implementation, pump inlet port 1203 may receive seals, such as o-ring seals, to seal the inlet nozzle of the pumping mechanism within the pump inlet port. In a second alternative implementation, pump inlet port 1203 may be received or housed concentrically within the pump inlet port of the pumping mechanism.

In another alternative implementation, pump inlet port 1203 may have a bonded connection to the manifold, or in yet another alternative implementation, manifold 120 may be manufactured or assembled in such a way that the pumping mechanism is integral to the manifold, and no ports exist as visible between two separate and distinct objects which can be discernably labelled "the pump" and "the manifold", meaning that any items in a pumping mechanism, such as a motor, piston, bellows, screw vane, gear pump, or other pumping means, are installed piece-wise into a manifold designed to receive the parts of a pump as individual components.

1.20.4 Hydraulic Circuit: Pump Outlet Port

In a preferred embodiment, manifold 120 may include a pump outlet port 1204 fluidly coupled in series to the outlet of a pumping mechanism for pumping working fluid. Pump outlet port 1204 may function to fluidly couple manifold 120 to an outlet nozzle of a pumping mechanism for pumping working fluid. In a first implementation, pump outlet port 1204 may include a cylindrical wall for housing the outlet nozzle of the pumping mechanism concentrically within the cylindrical wall. In such an implementation, pump outlet port 1204 may receive seals, such as o-ring seals, to seal the outlet nozzle of the pumping mechanism within the pump outlet port. In a second alternative implementation, pump outlet port 1204 may be received or housed concentrically within the pump outlet port of the pumping mechanism. Additionally, or alternatively, any or all of the methodologies previously discussed as beneficial or possible to use on the pump inlet port 1203 could additionally or alternatively be used in the pump outlet port 1204.

1.20.5 Hydraulic Circuit: First Pump Outlet Chamber

In a preferred embodiment, manifold 120 may include a first pump outlet chamber 1205 fluidly coupled in series to the pump outlet port 1204. In such a preferred embodiment, first pump outlet chamber 1205 may function to receive a flow of working fluid from the pumping mechanism of male prosthetic device 100 and guide the flow to other components of manifold 120 serially downstream of first pump outlet chamber 1205. In an implementation, first pump outlet chamber 1205 may be defined by a cylindrical wall with an opening to one or more downstream fluid chambers and/or passages.

In some embodiments, first pump outlet chamber 1205 may also function to house a check valve for preventing a backflow of working fluid into the outlet of the pumping mechanism. While such a check valve system may not be necessary in every embodiment, one skilled in the art may recognize that within a battery powered device, if there is a non-zero leakage of fluid back through the pump which must be resisted by intermittently running the pump, including such a check valve within the pump outlet flow path may result in significant power savings and an enhancement in the usability of the device. One embodiment to create a robust and low-cost check valve is may include a bearing ball and spring in-line with a pump outlet flow path, such that when the pumping mechanism is turned on the fluid pressure may move the ball by compressing the spring, but when pump flow is turned off, the spring may seat the ball in place on a pump outlet port and differential fluid pressure on opposite sides of the ball may complete a seal preventing flow into a pump outlet port. As pumping against a spring force may cause a battery-operated pump to draw more power, the spring rate may be contemplated to be a low as possible, and both the spring and bearing ball may be contemplated to be made of material which may not corrode when in use within the working fluid. In another alternative implementation, another suitable one-way check valve system maybe be utilized, such as a duckbill valve, a plate valve, or any other suitable fluidic check valve.

1.20.6 Hydraulic Circuit: Second Pump Outlet Chamber

In a preferred embodiment, manifold 120 may include a second pump outlet chamber 1206 fluidly coupled in series to the first pump outlet chamber 1205. In such a preferred embodiment, second pump outlet chamber 1206 may function to receive a flow of working fluid from the first pump outlet chamber 1205 and guide the flow to other components of manifold 120 serially downstream of second pump outlet chamber 1206. In an embodiment, second pump outlet chamber 1206 may be adjacent first pump outlet chamber 1205. In such an embodiment, second pump outlet chamber 1206 may receive a flow of working fluid from an opening in first pump outlet chamber 1205. In one embodiment, second pump outlet chamber 1206 may include an opening to an inlet of a fluid passage downstream of second pump outlet chamber 1206.

1.20.7 Hydraulic Circuit: Reservoir Inlet Passage

In a preferred embodiment, manifold 120 may include a reservoir inlet passage 1207 that may function to carry fluid from one or more upstream pump outlet chambers to a downstream reservoir. In an implementation, reservoir inlet passage 1207 may be fluidly coupled in series to an outlet of second pump outlet chamber 1206. In such an implementation, an inlet of reservoir inlet passage 1207 may be arranged at an opening on a wall of second pump outlet chamber 1206. Preferably, reservoir inlet passage 1207 may include an outlet to an opening of a downstream reservoir. In an implementation, reservoir inlet passage 1207 may include an outlet to an opening of expansible reservoir 140. In an alternative implementation, manifold 120 may include more than one parallel reservoir inlet passage 1207 fluidly coupled between one or more upstream pump outlet chambers and a downstream reservoir.

1.20.8 Hydraulic Circuit: Reservoir Outlet Ports

In a preferred embodiment, manifold 120 may include one or more reservoir outlet ports 1208 that may function to carry or drain a flow of working fluid from an upstream reservoir to one or more downstream components of male prosthetic device 100. Preferably, the one or more reservoir outlet ports 1208 may each be fluidly coupled serially downstream from the upstream reservoir, and the one or more reservoir outlet ports 1208 may each be fluidly coupled serially upstream from a reservoir outlet passage. In such an implementation, each of the one or more reservoir outlet ports 1208 may deliver fluid in parallel relative to one another (i.e., each reservoir outlet port 1208 may be arranged in parallel in a hydraulic circuit). Each reservoir outlet port 1208 may include an inlet at an opening of the upstream reservoir for receiving the flow of working fluid, and each reservoir outlet port 1208 may include an outlet at the downstream reservoir outlet passage. In a preferred implementation, the one or more reservoir outlet ports 1208 may include at least three outlet ports 1208. Such an implementation may allow for redundancy in the event of partial and/or complete blockage of an outlet port 1208. In operation of a preferred embodiment, the one or more reservoir outlet ports 1208 may direct fluid from the reservoir upstream to a reservoir outlet passage 1209 downstream.

1.20.9 Hydraulic Circuit: Reservoir Outlet Passage

In a preferred embodiment, manifold 120 may include a reservoir outlet passage 1209 that may function to carry fluid from one or more upstream ports to one or more downstream valve chambers. In an implementation, reservoir outlet passage 1209 may be fluidly coupled in series to and downstream of the one or more reservoir outlet ports 1208. In such an implementation, inlets of reservoir outlet passage 1209 may be arranged at locations where reservoir outlet ports 1208 intersect reservoir outlet passage 1209. Preferably, reservoir outlet passage 1209 may include an outlet to an opening of a downstream valve chamber. In an implementation, reservoir outlet passage 1209 may include an outlet to an opening of valve inlet chamber 1210.

1.20.10 Hydraulic Circuit: Valve Inlet Chamber

In a preferred embodiment, manifold 120 may include a valve inlet chamber 1210 that may function to allow a flow of working fluid from one or more upstream fluid passages to an inlet of an electromechanical valve. Additionally, valve inlet chamber 1210 may also function to house the inlet nozzle of the electromechanical valve concentrically within valve inlet chamber 1210. In one embodiment, valve inlet chamber 1210 may include a lower cylindrical wall for housing the inlet nozzle of the electromechanical valve, and an upper frustoconical wall for receiving a flow of working fluid from upstream fluid passages. Valve inlet chamber may include one or more seals, such as o-ring seals, arranged concentrically within the lower cylindrical wall for sealing the valve inlet chamber. In operation of a preferred embodiment, working fluid may flow from reservoir outlet passage 1209 into valve inlet chamber 1210, and may further flow from valve inlet chamber 1210 into an inlet of the electromechanical valve when the electromechanical valve is open.

1.20.11 Hydraulic Circuit: Valve Outlet Chamber

In a preferred embodiment, manifold 120 may include a valve outlet chamber 1211 that may function to allow a flow of working fluid from one or more outlets of an electromechanical valve to one or more downstream fluid passages. In one embodiment, valve outlet chamber 1211 may include a lower cylindrical wall adjacent one or more outlets of the electromechanical valve, and an upper frustoconical wall. The lower cylindrical wall and the upper frustoconical wall together may define a volume of the valve outlet chamber 1211 for receiving a flow of working fluid from the one or more outlets of the electromechanical valve. In a preferred embodiment, valve outlet chamber 1211 may include a tangential opening or outlet to a downstream fluid passage. In operation of a preferred embodiment, when the electromechanical valve is open, working fluid may flow from the one or more outlets of the electromechanical valve into valve outlet chamber 1211, and may further flow from valve outlet chamber 1211 through the tangential outlet of valve outlet chamber 1211 to reservoir exchange passage 1212 downstream.

1.20.12 Hydraulic Circuit: Reservoir Exchange Passage

In a preferred embodiment, manifold 120 may include a reservoir exchange passage 1212 that may function to carry fluid from an upstream valve chamber to one or more downstream chambers. In an implementation, reservoir exchange passage 1212 may be fluidly coupled in series to and downstream of valve outlet chamber 1211, and reservoir exchange passage 1212 may be fluidly coupled in series to and upstream of reservoir exchange chamber 1201. In such an implementation, an inlet of reservoir exchange passage 1212 may be arranged at a tangential outlet or opening of valve outlet chamber 1211, and an outlet of reservoir exchange passage 1212 may be arranged on at least one wall of reservoir exchange chamber 1201. In operation of a preferred embodiment, when the electromechanical valve is open, working fluid may flow from the upstream valve outlet chamber 1211, through reservoir exchange passage 1212, downstream to reservoir exchange chamber 1201.

1.22 Flow-Regulating Manifold: Reservoir Coupling Hole

In a preferred embodiment, manifold 120 may include a reservoir coupling hole 122 that may function to mechanically and fluidly couple manifold 120 to a fluid reservoir. Preferably, reservoir coupling hole 122 may couple manifold 120 to source reservoir 110. In one embodiment, reservoir coupling hole 122 may include a cylindrical threaded hole on a lower surface of manifold 120. In such an embodiment, "lower" may refer to a direction along a central longitudinal axis of coupling hole 122 toward the reservoir, and "upper" may refer to a direction along the central longitudinal axis away from the reservoir. In a preferred implementation, coupling hole 122 may receive threaded coupling 116 of hydraulic coupling 115 to couple source reservoir 110 to manifold 120.

1.23 Flow-Regulating Manifold: Pump Housing Cavity

In a preferred embodiment, manifold 120 may include a pump housing cavity 123 that may function to house a pumping mechanism of male prosthetic device 100. In an embodiment, pump housing cavity 123 may include a cavity with an opening in an upper surface of manifold 120. In an embodiment, pump housing cavity 123 may include first, second, and third rectangular walls extending in a direction of a longitudinal axis of manifold 120, and a fourth rectangular wall extending in the direction of a longitudinal axis of manifold 120 to a lower height than the first, second, and third rectangular walls.

In some embodiments, pump housing cavity 123 may include a pump seat 1231 that may function to receive a pump inlet and a pump outlet of the pumping mechanism. Pump seat 1231 may include a protrusion or shelf on a wall of pump cavity 123. In such an embodiment, the shelf or wall of pump seat 1231 may extend perpendicularly to the fourth wall of pump cavity 123 at the top of the fourth wall of pump cavity 123. Preferably, pump inlet port 1203 and pump outlet port 1204 are arranged in pump seat 1231 to receive a pump inlet and a pump outlet respectively.

In a preferred embodiment, pump housing cavity 123 may include vibration-isolating strips or layers on walls of the pump housing cavity 123. The vibration-isolating strips or layers may function to isolate noise and vibrations of a pumping mechanism housed within pump housing cavity 123 from other components and/or a user of male prosthetic device 100. In some embodiments, a pumping mechanism housed in pump housing cavity 123 may only directly contact the vibration-isolating strips or layers of pump housing cavity 123 without directly contacting the walls of pump housing cavity 123 and/or manifold 120. In some embodiments, the vibration-isolating strips or layers may be vibration-isolating foam strips or layers.

An alternative embodiment may be envisioned where all components of the pumping mechanism, such as motors, wires, gears, and pump system, may be individually integrated into the housing manifold itself, such that the pumping mechanism and manifold 120 are not distinct individual components.

1.24 Flow-Regulating Manifold: Reservoir Coupling Protrusion

Figure 8:
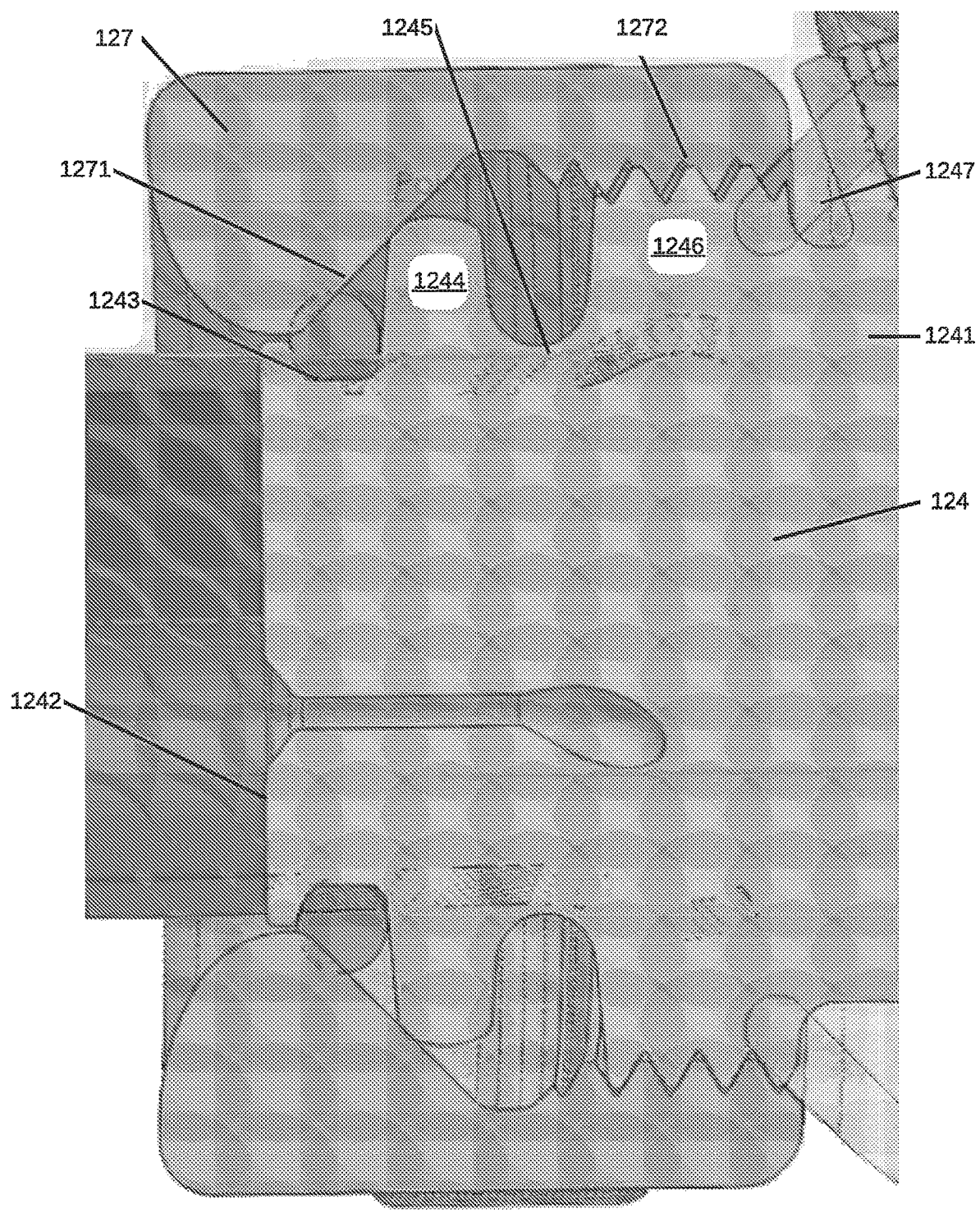
FIG. 8 illustrates a first embodiment of a reservoir coupling protrusion of a manifold of a phallus prosthetic device in accordance with one or more embodiments of the present application.
Figure 9:
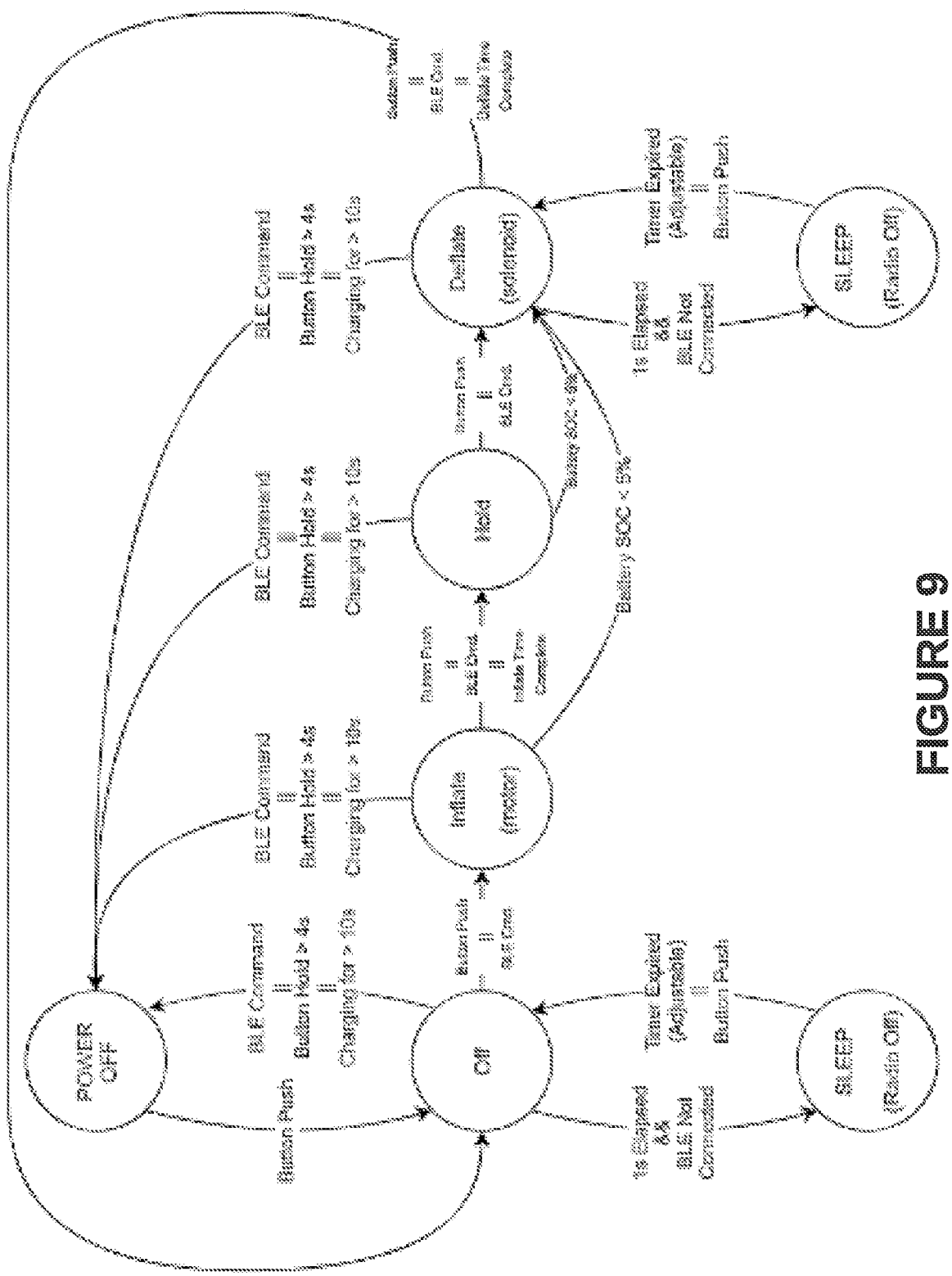
FIG. 9 illustrates an example schematic of a state diagram of a phallus prosthetic device in accordance with one or more embodiments of the present application.
Figure 10:
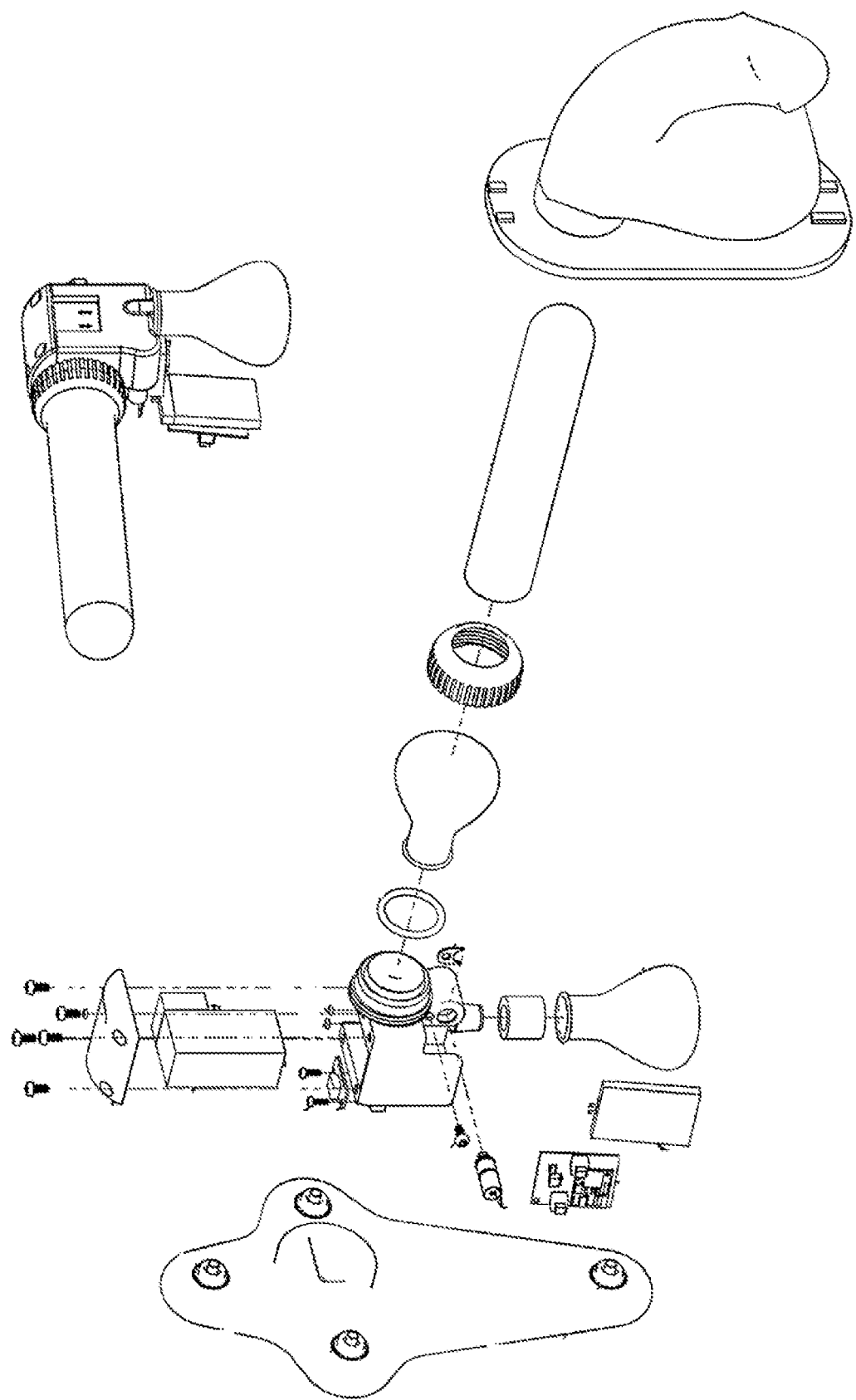
FIG. 10 illustrates a second embodiment of a phallus prosthetic device in accordance with one or more embodiments of the present application.

In a preferred embodiment, manifold 120 may include a reservoir coupling protrusion 124 that may function to mechanically and fluidly couple manifold 120 to a fluid reservoir, as shown by way of example in FIG. 8. Preferably, reservoir coupling protrusion 124 may couple manifold 120 to expansible reservoir 140. In a preferred embodiment, reservoir coupling protrusion 124 may extend perpendicularly from a planar outer wall of manifold 120, and reservoir coupling protrusion 124 may extend from a base 1241 to an end face 1242. In some embodiments, reservoir coupling protrusion 124 may include a sealing groove 1243, a securing lip 1244, a securing groove 1245, a threaded section 1246, and a sleeve-securing gap 1247. In operation of a preferred embodiment, reservoir coupling protrusion 124 may engage with a securing cap 127 to secure a portion of the reservoir concentrically between reservoir coupling protrusion 124 and securing cap 127.

1.24.1 Reservoir Coupling Protrusion: Base and End Face

In a preferred embodiment, reservoir coupling protrusion 124 may extend or protrude from an outer wall of manifold 120. In such a preferred embodiment, an outer circumferential surface of reservoir coupling protrusion 124 may extend around a coupling protrusion longitudinal axis perpendicular to a plane that the outer wall of manifold 120 lies within. In some embodiments, a section of the reservoir coupled by coupling protrusion 124 may be arranged or located radially outward of the outer circumferential surface of reservoir coupling protrusion 124. Reservoir coupling protrusion 124 may extend in a direction along the coupling protrusion longitudinal axis from a base 1241 at the outer wall of manifold 120 to an end face 1242 distal from the outer wall of manifold 120. In some embodiments, an outlet of reservoir inlet passage 1207 (described in section 1.21.7 above) and the inlets of reservoir outlet ports 1208 (described in 1.21.8 above) may be arranged on end face 1242 of reservoir coupling protrusion 124.

1.24.3 Reservoir Coupling Protrusion: Sealing Groove

In a preferred embodiment, reservoir coupling protrusion 124 may include a sealing groove 1243 that may function to receive a sealed section of the coupled reservoir and a circumferential seal (e.g., an o-ring seal). In such a preferred embodiment, the sealed section of the coupled reservoir may be compressed between the circumferential seal and the sealing groove 1243. In some embodiments, sealing groove 1243 may be on and/or part of the outer circumferential surface of reservoir coupling protrusion 124. In such embodiments, sealing groove 1243 may be adjacent end face 1242 of reservoir coupling protrusion 124, and may have a minimum groove outer radius smaller than an outer radius of end face 1242 relative to the longitudinal axis of coupling protrusion 124.

1.24.4 Reservoir Coupling Protrusion: Securing Lip and Securing Groove

In a preferred embodiment, reservoir coupling protrusion 124 may include a securing lip 1244 and a securing groove 1245 that may function to secure an end section of the coupled reservoir. In such a preferred embodiment, the end section of the coupled reservoir may be arranged on or around an outer circumferential surface of securing lip 1244 and securing groove 1245. In some embodiments, securing lip 1244 and securing groove 1245 may be on and/or part of the outer circumferential surface of reservoir coupling protrusion 124. In such embodiments, securing lip 1244 may be located axially between sealing groove 1243 and securing groove 1245 along the longitudinal axis of coupling protrusion 124, such that securing lip 1244 may be closer to end face 1242 than securing groove 1245. Preferably, relative to the longitudinal axis of coupling protrusion 124, securing lip 1244 may have a maximum lip outer radius larger than each of: an outer radius of end face 1242, a minimum groove outer radius of sealing groove 1243, and a minimum groove outer radius of securing groove 1245. Preferably, relative to the longitudinal axis of coupling protrusion 124, securing groove 1245 may have a minimum groove outer radius larger than a minimum groove outer radius of sealing groove 1243.

1.24.6 Reservoir Coupling Protrusion: Threaded Section

In a preferred embodiment, reservoir coupling protrusion 124 may include a threaded section 1246 that may include threads that may function to cooperate with threads on a securing cap threaded on an outer circumference of coupling protrusion 124. In some embodiments, threaded section 1246 may be a threaded outer circumferential surface of reservoir coupling protrusion 124. In such embodiments, threaded section 1246 may be axially adjacent securing groove 1245, axially closer to base 1241 of coupling protrusion 124 than securing groove 1245 along the longitudinal axis of coupling protrusion 124. Preferably, relative to the longitudinal axis of coupling protrusion 124, threaded section 1246 may include a maximum outer radius larger than a maximum lip outer radius of securing lip 1244 such that securing groove 1245 is formed axially between securing lip 1244 and threaded section 1246.

1.24.7 Reservoir Coupling Protrusion: Sleeve Securing Gap

In a preferred embodiment, reservoir coupling protrusion 124 may include a sleeve securing gap 1247 that may function to secure a sleeve to coupling protrusion 124. In such a preferred embodiment, a sleeve may be arranged around (i.e., concentrically around) coupling protrusion 124, and an end of the sleeve may be received in and/or secured by sleeve securing gap 1247. In some embodiments, sleeve securing gap 1247 may be a gap on the outer circumferential surface of reservoir coupling protrusion 124. In such embodiments, sleeve securing gap 1247 may be adjacent base 1241, axially between base 1241 and threaded section 1246 along the longitudinal axis of coupling protrusion 124. Sleeve securing gap 1247 may be defined by a groove formed between base 1241 and threaded section 1246.

1.27 Reservoir Coupling Protrusion: Securing Cap

In a preferred embodiment, male prosthetic device 100 may include a securing cap 127 that may function to cooperate or engage with reservoir coupling protrusion 124 to secure a portion of the reservoir concentrically between reservoir coupling protrusion 124 and securing cap 127. In an embodiment, securing cap 127 may be arranged concentrically around reservoir coupling protrusion 124. Preferably, securing cap 127 may include a tapered surface 1271 and a threaded surface 1272. In such a preferred embodiment, tapered surface 1271 may be arranged closer to end face 1242 of coupling protrusion 124 than threaded surface 1272, in an axial direction of the longitudinal axis of coupling protrusion 124. Preferably, tapered surface 1271 and threaded surface 1272 are part of an inner circumferential surface of securing cap 127.

In a preferred embodiment, tapered surface 1271 may be tapered such that, when arranged around coupling protrusion 124, an end of tapered surface 1271 closest to end face 1242 of coupling protrusion 124 in an axial direction of the longitudinal axis of coupling protrusion 124 may be closer to the longitudinal axis than an end of tapered surface 1271 farthest away from end face 1242 of coupling protrusion 124 in an axial direction of the longitudinal axis. Preferably, tapered surface 1271 may be tapered such that, when securing cap 127 is secured on coupling protrusion 124, at least a portion of tapered surface 1271 engages and compresses the circumferential seal arranged in sealing groove 1243 of reservoir coupling protrusion 124.

In a preferred embodiment, threaded surface 1272 may function to engage with threaded section 1246 of coupling protrusion 124 to secure cap 127 to coupling protrusion 124. Preferably, threaded surface 1272 may include threads on an inner circumferential surface of securing cap 127, such that securing cap 127 may be threaded onto an outer circumferential surface of coupling protrusion 124.

1.30 Male Prosthetic Device: Pump

In a preferred embodiment, pump 130 of male prosthetic device 100 may function to provide a one-way flow of working fluid in at least one hydraulic circuit of male prosthetic device 100. Preferably, pump 130 may be arranged and/or housed in manifold 120. In a preferred embodiment, pump 130 may include a pump body 131, a pump inlet 132 fluidly connected to manifold 120 and a pump outlet 133 fluidly connected to manifold 120. In some embodiments, pump 130 may function as a one-directional pump, i.e., pump 130 may only drive fluid in one direction from pump inlet 132 to pump outlet 133.

In a preferred embodiment, pump 130 may include a pump body 131 that may be housed within manifold 120. In an implementation, pump body 131 may be housed within pump housing cavity 123. In such an implementation, pump inlet 132 and/or pump outlet 133 may be received on pump seat 1231 of pump housing cavity 123 (described in section 1.23 above).

In a preferred embodiment, pump 130 may include a pump inlet 132 and a pump outlet 133. In some embodiments, pump inlet 132 may be a pump inlet nozzle, and/or pump outlet 133 may be a pump outlet nozzle. In such embodiments, the pump inlet nozzle of pump inlet 132 and/or the pump outlet nozzle of pump outlet 133 may be received in pump inlet port 1203 and pump outlet port 1204 respectively (described in sections 1.20.3 and 1.20.4 above).

In an alternative embodiment, pump 130 may be a bi-directional pump 130b which may be controlled to provide flow in both directions. In such an alternative embodiment, pump 130b may function as a bi-directional pump to provide a flow from a source reservoir nob to an expansible reservoir 140b in one direction, and a flow from expansible reservoir 140b to source reservoir nob in a second direction, as shown by way of example in FIG. 5B. Such an alternative embodiment may result in the use of a potentially more expensive pump but also may enable a reduction in the number of components in male prosthetic device 100, by reducing or eliminating the need for an electromechanical valve.

It should be noted that in a preferred embodiment, hydraulic system of prosthetic device 100 and pump 13c, do not provide pulsation or hydraulically-driven vibrating massage during use. While one might contemplate several ways to enhance a sexual act with novel uses of the current mechanical components, the hydraulic system of this device is intended to allow the phallus prosthetic to become erect when desired, and flaccid when desired.

1.40 Male Prosthetic Device: Expansible Reservoir

In a preferred embodiment, male prosthetic device 100 includes an expansible reservoir 14c, that may function to receive, hold, and discharge working fluid. Preferably, expansible reservoir 14c, may function to expand when receiving a flow of working fluid, and contract when discharging a flow of working fluid. Expansible reservoir 14c, may be mechanically and fluidly coupled to manifold 120. In a preferred embodiment, expansible reservoir 140 may be a flexible reservoir made of an elastomeric material.

Preferably, expansible reservoir 14c, may function to receive a flow of fluid in an actively expanding state of male prosthetic device 100. In an operation of some preferred embodiments, expansible reservoir 14c, may receive and/or store a volume of fluid in an active and/or expanded state of male prosthetic device 100 that is greater than a volume of fluid stored by expansible reservoir 14c, in a rest and/or unexpanded state of male prosthetic device 100. In a preferred embodiment, expansible reservoir 14c, may function to drain or supply fluid from expansible reservoir 140 in a contracting state of male prosthetic device 100.

In an implementation, expansible reservoir 140 may be made of a flexible or resilient material, such as an elastomeric material. In some embodiments, expansible reservoir 140 may be a flexible balloon-type reservoir.

Preferably, expansible reservoir 140 may include an opening 141 that allows bi-directional fluid flow into and out of expansible reservoir 140. In one implementation, opening 141 may be at an end of expansible reservoir 140 that may be mechanically and fluidly coupled to manifold 120. In an implementation, an end of expansible reservoir 140 may be mechanically and fluidly coupled to manifold 120 by reservoir coupling protrusion 124 of manifold 120 (described in section 1.24 above).

Preferably, expansible reservoir 140 and source reservoir 110 may be sized relative to one another such that each reservoir has a size and/or volume based on the other reservoir. For example, in a preferred embodiment, expansible reservoir 140 may have a volume at rest (i.e., in an unexpanded or rest state) that is lower than a volume of source reservoir 110 at rest. In such a preferred embodiment, the relative sizing of expansible reservoir 140 and source reservoir 110 may function to advantageously produce or ensure a draining flow from expansible reservoir 140 to source reservoir 110 by a contraction of expansible reservoir 140, without requiring the use of a pumping mechanism. That is, when expansible reservoir 140 is in an expanded state, and a fluid pathway is open between expansible reservoir 140 and source reservoir 110, expansible reservoir 140 may contract to drive a flow of fluid out of expansible reservoir 140 and into source reservoir 110.

It shall be noted that, in a preferred embodiment described herein, all fluid may be retained within the prosthetic device 100, and the device may be designed such that no leaks are present. It may be contemplated that some lubrication might be desired while using the device, and in an alternative embodiment such lubrication may be enabled by yet another reservoir. Such a lubricant or additional reservoir may be completely separate and segregated from the working fluid system, and may require a separate pumping system, as a secondary fluid, perhaps for lubrication, may be completely segregated from the fluid system used to hydraulically switch between flaccid (i.e., contracted) and erect (i.e., expanded) states of expansible reservoir 140.

1.50 Male Prosthetic Device: Check Valve

In a preferred embodiment, male prosthetic device 100 includes check valve 150 that may function to prevent a flow of working fluid into the pump outlet of the pumping mechanism of male prosthetic device 100. In such a preferred embodiment, check valve 150 may be arranged fluidly downstream of the pump outlet. Preferably, check valve 150 is housed within manifold 120.

Preferably, check valve 150 may be arranged inside first pump outlet chamber 1205 of manifold 120. In an embodiment, check valve 150 may include a spring 151 and a ball 152. In such an embodiment, the spring 151 may be oriented with a compression/extension axis parallel to a longitudinal axis of first pump outlet chamber 1205. Spring 151 may force ball 152 upwards towards the pump outlet, as shown by way of example in FIG. 6A. A fluid flow from the pump outlet may push downwards against ball 152, causing a downward compression of spring 151, as shown by way of example in FIG. 6B.

1.60 Male Prosthetic Device: Electromechanical Valve

In a preferred embodiment, electromechanical valve 160 of male prosthetic device 100 may function to selectively control fluid flow in a hydraulic circuit of male prosthetic device 100. In an implementation, electromechanical valve 160 may function to control a flow in hydraulic circuit 1200 of manifold 120. In a preferred embodiment, electromechanical valve 160 may include an inlet nozzle 161 and one or more outlets 162. Preferably, electromechanical valve 160 is housed within manifold 120. In some implementations, electromechanical valve 160 may be a solenoid valve.

In an implementation, electromechanical valve 160 may function to control flow from expansible reservoir 140 to source reservoir 110. In such a preferred embodiment, electromechanical valve 160 may be closed to prevent flow from expansible reservoir 140 to source reservoir 110, and electromechanical valve 160 may be opened to allow flow from expansible reservoir 140 to source reservoir 110. Preferably, electromechanical valve 160 is housed in manifold 120, and electromechanical valve 160 is preferably arranged fluidly downstream of expansible reservoir 140.

In a preferred embodiment, electromechanical valve 160 may include an inlet nozzle 161 that may function to receive a flow of fluid from one or more upstream components of male prosthetic device 100 when electromechanical valve 160 is in an open state. In some embodiments, inlet nozzle 161 may include an axial inlet opening relative to a longitudinal axis of electromechanical valve 160. In an implementation of a preferred embodiment of male prosthetic device 100, inlet nozzle 161 may be housed within valve inlet chamber 1210 of manifold 120.

In a preferred embodiment, electromechanical valve 160 may include one or more outlets 162 that may function to discharge a flow of fluid from electromechanical valve 160 when electromechanical valve 160 is in an open state. In some embodiments, the one or more outlets 162 may be arranged to discharge fluid in an axial direction relative to the longitudinal axis of the electromechanical valve 160. In an implementation of a preferred embodiment of male prosthetic device 100, the one or more outlets 162 may be arranged within valve outlet chamber 1211 of manifold 120.

In operation of a preferred embodiment, electromechanical valve 160 may be closed to prevent an outflow of fluid from expansible reservoir 140. In such an embodiment, electromechanical valve 160 may be closed in an expanding and/or an expanded hold state of male prosthetic device 100. In operation of a preferred embodiment, electromechanical valve 160 may be opened to allow a drainage or outflow of fluid from expansible reservoir 140. In such an embodiment, electromechanical valve 160 may be opened in a contracting and/or a rest state of male prosthetic device 100.

1.70 Male Prosthetic Device: Battery

In a preferred embodiment, male prosthetic device 100 includes a battery 170 that may function to provide power to electrical components of male prosthetic device 100. In such a preferred embodiment, battery 170 may function as a power source for pump 130, electromechanical valve 160, and controller 200. Battery 170 is preferably housed in manifold 120.

1.80 Male Prosthetic Device: Sleeve

In a preferred embodiment, male prosthetic device 100 includes a sleeve 180 that may function to constrain or limit a size of expansible reservoir 140. In such a preferred embodiment, sleeve 180 may be arranged around expansible reservoir 140, and may be secured to manifold 120. Preferably, sleeve 180 may constrain a size of expansible reservoir 140 by limiting a maximum size of expansible reservoir 140 to a size of the sleeve 180 when expansible reservoir 140 is in an expanded state.

In a preferred embodiment, sleeve 180 may be arranged concentrically around expansible reservoir 140 to constrain a size and/or shape of expansible reservoir 140. In such a preferred embodiment, sleeve 180 may be secured to manifold 120. In an implementation of a preferred embodiment, sleeve 180 may be received in and secured to sleeve securing gap 1247 of reservoir coupling protrusion 124 (see section 1.24.7 above). Sleeve 180 may include a drawstring at an end of sleeve 180 that may be tightened to secure sleeve 180 on reservoir coupling protrusion 124.

Preferably, sleeve 180 may be made of a fabric material. Sleeve 180 may advantageously be made of a fabric material such as nylon, rayon, and/or polyester to prevent stretching and tearing of sleeve 180. In addition, such fabric materials may advantageously prevent deterioration and/or mold growth. Alternatively, sleeve 180 may be made from any material suitable to the operation of sleeve 180 in male prosthetic device 100. In an alternative preferred embodiment, such a fabric sleeve may be cast, impregnated, or made continuous with a material used to create an external phallus shape, which may be a flexible silicone material and may be over-molded in such a way that the sleeve 180 may be retained completely with that material.

1.90 Male Prosthetic Device: Manifold Cover

In a preferred embodiment, male prosthetic device 100 includes manifold cover 190 that may function to house controller 200. Preferably, manifold cover 190 is mechanically connected to manifold 120 by a hinge connection 192 and mechanical fasteners 193. In a preferred embodiment, manifold cover 190 may be arranged to cover an open top of manifold 120. In some embodiments, manifold cover 190 may cover pump 130 in pump housing cavity 123 of manifold 120. In such a preferred embodiment, manifold cover 190 may be opened and/or removed to allow access to pump 130. In some embodiments, manifold cover 190 may include a vibration-isolating strip or layer.

2.00 Male Prosthetic Device: Controller

In a preferred embodiment, male prosthetic device 100 includes controller 200 that may function to automatically transition male prosthetic device 100 between states including, but not limited to, an expanding state, a holding state, a contracting of 48 state, and a rest state. In such an embodiment, controller 200 may transition between states by automatically controlling components including, but not limited to, pump 130 and electromechanical valve 160. In an embodiment, controller 200 may execute conditional state transitions, as shown by way of example in FIG. 9. In a preferred embodiment, controller 200 may include a wireless module that may function to receive user input. Controller 200 may preferably be housed within manifold cover 190.

Controller 200 may also include at least one button which may be interacted with by physical touch and may allow control of the prosthetic device 100 and change of state or modes of the prosthetic device 100 by pressing the button, as a duplicative and/or additional method of control versus a wireless means of control.

The wireless module of controller 200 may preferably be in communication with a hand-held device and may be in continuous or intermittent communication with such a hand-held device. The wireless module may respond to commands from the hand-held device to change states or modes, and the wireless module may additionally or alternatively report to the hand-held device many parameters, including but not limited to: erect state, battery state, wireless communication state, hours of use, pumping cycles, serial number of unit, etc.

Controller 200 may include an electronics package that may include at least one LED that may function to give visible feedback to the wearer, such as about a Bluetooth® status, a state of charge, and/or a state of operation. Such an LED may be used intermittently or continuously to relay information to the user. In such an embodiment, a housing or protective enclosure for the electronics package may advantageously be constructed out of a clear plastic, such that the LED may be visible through the housing or protective enclosure.

In an embodiment, prosthetic device 100 may include at least one sensor, and/or an array of sensors. In a non-limiting example, prosthetic device 100 may advantageously include temperature and/or fluid pressure sensors. In such an embodiment, feedback from the at least one sensor and/or the array of sensors may be integrated into controller 200 and/or an additional control system. Prosthetic device 100 may also include humidity sensors, multiple methods of tactile feedback sensors, and any other suitable sensor for use in prosthetic device 100.

2.10 Male Prosthetic Device: Prosthetic Enclosure

In a preferred embodiment, male prosthetic device 100 includes prosthetic enclosure 210 that may function as an enclosure or housing for male prosthetic device 100. In such a preferred embodiment, prosthetic enclosure 210 may change shape as expansible reservoir 140 and sleeve 180 expand and contract. In some embodiments, prosthetic enclosure 210 may function in the form or shape of prosthetic or artificial male anatomy. In some embodiments, prosthetic enclosure 210 may be a silicone prosthetic enclosure. Prosthetic enclosure 210 may be designed in such a way as to enable continuous wearing of the device for a user as desired and may enable times of intimacy to take place without burdensome planning and retrieval and adornment of any other such devices.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention. [ooin] Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed:

1. An electro-mechanical phallus prosthetic device comprising:
    a source reservoir that, at rest, stores a liquid;
    a target reservoir that, in use, flexibly stores at least a portion of the liquid;
    a manifold housing including:
        a first chamber that includes a plurality of flow paths arranged between the source reservoir and the target reservoir that, in use, act as conduits that transport the liquid through the manifold housing; and
        a second chamber that houses an electro-mechanical pump that, in use, forces a movement of the liquid from the source reservoir through at least one inlet flow path of the plurality of flow paths to the target reservoir; and
    a prosthetic phallus appendage that houses the target reservoir, the manifold housing, and the source reservoir.

2. The device according to claim 1, wherein:
    the source reservoir is mechanically secured along a first side of the manifold housing; and
    the target reservoir is mechanically secured along a second side of the manifold housing that is perpendicular or substantially perpendicular to the first side.

3. The device according to claim 2, wherein, in use:
the source reservoir elastically deforms to provide the liquid into the first chamber of the manifold housing based on an application of the electro-mechanical pump; and
the target reservoir flexibly expands into a shaft of the prosthetic phallus appendage based on storing the liquid from the source reservoir.

4. The device according to claim 2, wherein
the plurality of flow paths includes one or more outlet flow paths comprising one or more tubular shapes that extend from one or more fluid outlets of the target reservoir to a fluid inlet of the source reservoir.

5. The device according to claim 4, wherein
when the manifold housing is in a normal state relative to a horizontal plane, the at least one inlet flow path is positioned at a height greater that is normal to the horizontal plane relative to a height of the one or more outlet flow paths.

6. The device according to claim 4, further comprising:
an electromechanical valve that is arranged between the one or more fluid outlets of the target reservoir and the fluid inlet of the source reservoir.

7. The device according to claim 1, wherein
the prosthetic phallus appendage comprises a plurality of parts.

8. The device according to claim 1, further comprising:
a first aperture between the first chamber and the second chamber that receives a pump inlet of the electro-mechanical pump; and
a second aperture between the first chamber and the second chamber that receives a pump outlet of the electro-mechanical pump.

9. The device according to claim 8, wherein
the first aperture and the second aperture are arranged along a same chamber wall between the first chamber and the second chamber.

10. The device according to claim 8, further comprising:
a check valve that is arranged between the pump outlet of the electro-mechanical pump and the at least one inlet flow path to the target reservoir.

11. The device according to claim 1, further comprising:
a fabric sheath that extends from a fluid inlet of the target reservoir and that encompasses a body of the target reservoir.

12. The device according to claim 11, wherein
a proximal end of the fabric sheath is secured to the manifold housing via a circumferential lip of a circumferential spout extending from a body of the manifold housing.

13. The device according to claim 1, wherein
the manifold housing comprises a single three-dimensionally printed continuously integrated component.

14. The device according to claim 1, wherein
the at least one inlet flow path comprises a tubular shape that extends from a pump outlet to a fluid inlet of the target reservoir.

15. The device according to claim 14, wherein
the plurality of flow paths includes a plurality of outlet flow paths, wherein each of the plurality of outlet flow paths comprises a tubular shape, the plurality of outlet flow paths extending from one or more fluid outlets of the target reservoir merge at a point within the manifold housing to form a single outlet flow path to at least one fluid inlet of the source reservoir.

16. The device according to claim 1, further comprising:
a manifold lid that is mechanically secured to the manifold housing and that covers the second chamber of the manifold housing.

17. The device according to claim 1, wherein
the electro-mechanical pump when arranged within the second chamber of the manifold housing, a pump inlet and a pump outlet are engaged with a first aperture and a second aperture creates a one-way fluid channel that passes liquid from the source reservoir to the target reservoir.

18. A device comprising:
a source reservoir that, at rest, stores a liquid, wherein the source reservoir is mechanically coupled along a first side of a manifold housing;
a target reservoir that, in use, flexibly stores at least a portion of the liquid and expands along an extent of a shaft based on the portion of the liquid that is stored within the target reservoir;
the manifold housing including:
  a first chamber that includes a plurality of flow paths arranged between the source reservoir and the target reservoir that, in use, move the liquid through the manifold housing; and
  a second chamber that houses an electro-mechanical pump that, in use, forces a movement of the liquid from the source reservoir through a source flow path of the plurality of flow paths to the target reservoir; and
a prosthetic appendage that houses the target reservoir, the manifold housing, and the source reservoir.

19. The device according to claim 18, wherein
the source flow path extends from a pump outlet of the electro-mechanical pump to a fluid inlet of the target reservoir.

20. The device according to claim 19, wherein
the plurality of flow paths includes one or more drainage flow paths that extend from one or more fluid outlets of the target reservoir to a fluid inlet of the source reservoir.

21. A device comprising:
a source reservoir that, at rest, stores a liquid, wherein the source reservoir is mechanically coupled along a first side of a manifold housing;
a target reservoir that, in use, flexibly stores at least a portion of the liquid and expands along an extent of a shaft based on the portion of the liquid that is stored within the target reservoir;
the manifold housing including:
  a first chamber that includes a plurality of flow paths arranged between the source reservoir and the target reservoir that, in use, move the liquid through the manifold housing; and
  multiple independent or connected chambers or orifices that house individual components of an electro-mechanical pump, comprising an electric motor, gears, shafts, and a suction chamber or a hydraulic working chamber, that, in use, forces a movement of the liquid from the source reservoir through a source flow path of the plurality of flow paths to the target reservoir; and
a prosthetic appendage that houses the target reservoir, the manifold housing, and the source reservoir.

* * * * *